(12) United States Patent
Zaaijer

(10) Patent No.: US 12,400,732 B1
(45) Date of Patent: Aug. 26, 2025

(54) METHODS, APPARATUSES, AND TOOLS FOR SEMI-AUTOMATED DIGITAL SUPPORT AND STRUCTURED DATA CAPTURE FOR THE MULTI-DIMENSIONAL MANUAL PROCESS OF CELL CULTURE MAINTENANCE AND MANIPULATION ENABLING ARTIFICIAL INTELLIGENCE (AI) DRIVEN PREDICTION AND CONTROLLED DATA SHARING

(71) Applicant: The Joan and Irwin Jacobs Technion-Cornell Institute, New Rochelle, NY (US)

(72) Inventor: Sophie Zaaijer, Riverside, CA (US)

(73) Assignee: The Joan and Irwin Jacobs Technion-Cornell Institute, New Rochelle, NY (US)

( * ) Notice: Subject to any disclaimer, the term of this patent is extended or adjusted under 35 U.S.C. 154(b) by 0 days.

(21) Appl. No.: 18/353,829

(22) Filed: Jul. 17, 2023

Related U.S. Application Data

(60) Provisional application No. 63/389,586, filed on Jul. 15, 2022.

(51) Int. Cl.
  *G01N 33/48* (2006.01)
  *G16B 10/00* (2019.01)

(52) U.S. Cl.
  CPC .................................. *G16B 10/00* (2019.02)

(58) Field of Classification Search
  None
  See application file for complete search history.

(56) References Cited

U.S. PATENT DOCUMENTS

| | | |
|---|---|---|
| 2011/0269154 A1 | 11/2011 | Fantl et al. |
| 2019/0256924 A1 | 8/2019 | Vogelstein et al. |
| 2020/0167914 A1 | 5/2020 | Stamatoyannopoulos et al. |
| 2021/0217486 A1 | 7/2021 | Zaaijer et al. |

FOREIGN PATENT DOCUMENTS

WO  WO-2019113499 A1  6/2019

OTHER PUBLICATIONS

Selznick, Sanford H., et al. "Development and application of computer software for cell culture laboratory management." In Vitro Cellular & Developmental Biology-Animal 37.1 (2001): 55-61.*
Viader-Llargués, Oriol, et al. "Live cell-lineage tracing and machine learning reveal patterns of organ regeneration." Elife 7 (2018): e30823.*
Ben-David, U., et al., "Genetic and transcriptional evolution alters cancer cell line drug response", Nature. Aug. 2018; 560(7718): 325-330.
International Search Report and Written Opinion for International Application No. PCT/US2020/065084, mailed Mar. 19, 2021, 10 pgs.
Zaaijer, S., et al., "Tracking cell lineages to improve research reproducibility", Nat Biotechnol. May 19, 2021; 6(39): 666-670.

* cited by examiner

*Primary Examiner* — Anna Skibinsky
(74) *Attorney, Agent, or Firm* — COOLEY LLP

(57) ABSTRACT

A method includes generating a first node of a directed tree. The first node digitally represents a first cell population of a cell line. The method further includes receiving an indication from a user of a protocol to be performed on the first cell population that will generate a second cell population of the cell line. The method further includes generating a second node of the directed tree after the user has performed the protocol on the first cell population to generate the second cell population. The second node is automatically assigned as (1) a child node of the first node and (2) digitally represents the second cell population. The first node is connected to the second node in the directed tree via an edge. The method further includes causing, data to be stored at the edge. The data is a transformation of the protocol used to generate the second cell population. This structured cell associated data can be used to train AI algorithms to predict how protocol steps affect cell behavior (cell morphology, viability, fitness, cell-cell interactions, protein/compound production, expression profiles among other things).

21 Claims, 17 Drawing Sheets

GENERAL DATABASE

600

Generate a first node of a directed tree, the first node digitally representing a first cell population of a cell line 602

Receive an indication from a user of a protocol to be performed on the first cell population that will generate a second cell population of the cell line 604

Generate a second node of the directed tree, the second node (1) being a child node of the first node and (2) digitally representing the second cell population, the first node being connected to the second node in the directed tree via an edge 606

Cause, after the user has performed the protocol on the first cell population to generate the second cell population, data to be stored at the edge, the data being a transformation of the protocol used to generate the second cell population 608

Receive an indication that a user plans to generate a second cell population of a cell line based on a first cell population of the cell line, the first cell population digitally represented by a first node in a directed tree 702

↓

Send, automatically in response to receiving the indication that the user plans to generate the second cell population, a signal to cause display of a default protocol associated with the cell line 704

↓

Receive, based on input from the user, an indication of a change to the default protocol that generates a modified protocol 706

↓

Generate a second node that (1) is a child node of the first node, (2) is connected to the first node via an edge in the directed tree, and (3) digitally represents the second cell population 708

↓

Cause, after the user has performed the modified protocol on the first cell population, data associated with the modified protocol to be stored at the edge 710

Receive an indication that a user plans to generate a second cell population of a cell line based on a first cell population of the cell line, the first cell population digitally represented by a first node in a directed tree 802

Send, automatically in response to receiving the indication that the user plans to generate the second cell population, a signal to cause display of a default protocol associated with the cell line 804

Receive, based on input from the user, an indication that the default protocol will not be modified 806

Generate a second node that (1) is a child node of the first node, (2) is connected to the first node via an edge in the directed tree, and (3) digitally represents the second cell population 808

Cause, after the user has performed the default protocol on the first cell population, data associated with the default protocol to be stored at the edge 810

1202
1201

METHODS, APPARATUSES, AND TOOLS FOR SEMI-AUTOMATED DIGITAL SUPPORT AND STRUCTURED DATA CAPTURE FOR THE MULTI-DIMENSIONAL MANUAL PROCESS OF CELL CULTURE MAINTENANCE AND MANIPULATION ENABLING ARTIFICIAL INTELLIGENCE (AI) DRIVEN PREDICTION AND CONTROLLED DATA SHARING

CROSS-REFERENCE TO RELATED APPLICATION

This application claims priority to U.S. Provisional Patent Application No. 63/389,586, filed Jul. 15, 2022 and titled "METHODS, APPARATUSES, AND TOOLS FOR DIGITIZING THE MULTI-DIMENSIONAL PROCESS OF CELL CULTURE MAINTENANCE AND MANIPULATION ENABLING CONTROLLED DATA SHARING," the contents of which are incorporated by reference in its entirety herein. This application is related to U.S. patent application Ser. No. 16/740,327, filed Jan. 10, 2020 and titled "METHOD FOR MONITORING AND MANAGEMENT OF CELL LINES USING PERIODIC LOW-COVERAGE DNA SEQUENCING DATA", the contents of which are incorporated by reference in its entirety herein.

FIELD

One or more embodiments are related to methods, apparatuses, and tools for semi-automated digital support and structured data capture for the multi-dimensional manual process of cell culture maintenance and manipulation enabling artificial intelligence (AI) driven prediction and controlled data sharing.

BACKGROUND

The rise of cell-based innovation is driven by, for example, precision medicine initiatives using more diverse cell panels, CRISPR genome engineering, regenerative medicine, 3D cell models (organ-on-a-chip), organoid technology and/or the like. While the innovation in cell biology expands, the technology to support this innovation is lacking.

Current cell-related notes are dispersed and kept in separate silos and formats at various stages in the process of working with cell culture: 1) Pre-action: viewing protocols or Standard Operating Procedures (SOPs). Protocols and SOPs are instructional step-wise descriptions of actions to be performed in a laboratory to achieve a goal (e.g., passage a cell population, freeze cells, thaw cells, genetically engineer cells, etc.). The actions are typically performed in a specific order, with a specific quantity of specific reagents, for a specific cell line. Protocols are often saved in Word documents or PDFs. The digital PDFs are often stored in central data sharing places such as Google Drive, Dropbox, or Electronic Laboratory Notebooks (ELNs). 2) Post-action: capturing work that is performed on cells in the laboratory after the action is complete is done in, for example, paper notebooks, Electronics Notebooks (ELNs), spreadsheets like Excel, and/or the like. Notes can include reiterating the protocol steps post-action that are exactly replicated from the protocol listed pre-action, or capturing small modifications to the pre-action protocol done in response to the morphology of the cells the scientists observes. Cells are living entities that do not always behave consistently; modifications are therefore not uncommon and scientists often have to make case by case decisions. The cell-related work and note keeping will also include: observations of the cells, counting cells, making microscope images, and so on. The format of note keeping is not structured. Lastly 3) storing information about (long-term) inventory: stating what inventory there is in a lab, where tubes containing cells are stored in the freezer, what position inventory is in the freezer, what is done with spreadsheets such as Microsoft Excel, or Laboratory Information Management System (LIMS), and/or the like.

Linking these three data silos is complex and internally established methods within a single company or laboratory require training of their scientists on how this is done. Finding information about a protocol execution (e.g., notes about the specific protocol steps that are completed) that is performed six months ago by a colleague who left the laboratory——is highly complex and time-consuming if possible at all. This often requires cross referencing between the three data silos.

Protocols have a semi-standard format, but given their descriptive nature may not be immediately comparable. Note-keeping by scientists is non-standard: while some organizations state best practices, spontaneous observations or alterations in responses to biological phenomena are currently often non-predictable and therefore hard to standardize. Scientists make independent decisions on what to write down, in what order, and in what format. Inventory data is semi-standard (i.e., part of inventory tracking is standard). However, annotations can vary between laboratories and the level of information stored can vary between organizations. Therefore, due to the lack of standards, cell-associated data cannot always be shared easily from one person to another and/or viewed easily by a user(s). However, cell lines themselves are commonly shared from one person to the next.

Additionally, the three data capture phases (pre-action, post-action, inventory) lack easy and/or complete relationship data. The relationships between a cell line basics information (e.g., tissue of origin, age, ancestry, etc.), maintenance protocols/SOPs, actual experimental execution notes created by scientists over the duration the cell was in an in vitro state (over weeks, months, years), observations over this period on the cells to understand biology, and/or the like are currently rare if available at all.

As such, data extraction about sequential protocol execution steps (e.g., standard maintenance or experimental) in relation to observations of specific cell lines/lineages/strains over time (e.g., morphological, physiological, genetic), in relation with any other sequential repetitive operations or manipulation to cells over time can be cumbersome, if possible at all. This data, however, can be valuable for comparative analysis and longitudinal studies of cell line derived in vitro cell lineages (strains). It can be desirable, for example, to structure this data and use this data as input data to train AI/ML algorithms to create predictive models for improved decision making during the process of cell culture, for experimental design, and/or prediction of cell responses to certain imposed (treatment/genetic manipulation) regime. Additionally, such data extraction can be desirable for reproducibility in biomedical sciences, to gain, in some instances, novel scientific insights on the effect of human manipulation or interference (such as applying treatment or genetic manipulations) on cells grown in vitro, and eventually to understand longitudinal in vivo cellular responses to human induced interference. Moreover, the current lab specific data silos make retracing the history or provenance of a cell line difficult. This current lack of transparency can contribute to lack of trust in cell assets. Improving transparency can enhance trustworthiness and add value to these assets as the improved transparency improves reproducible science.

SUMMARY

In an embodiment, a method includes generating, at a processor, a first node of a directed tree. The first node digitally represents a first cell population of a cell line. The method further includes receiving, at the processor, an indication from a user of a protocol to be performed on the first cell population that will generate a second cell population of the cell line. The method further includes generating, at the processor, a second node of the directed tree. The second node (1) is a child node of the first node and (2) digitally represents the second cell population. The first node is connected to the second node in the directed tree via an edge. The method further includes causing, at the processor and after the user has performed the protocol on the first cell population to generate the second cell population, data to be stored at the edge. The data is a transformation of the protocol used to generate the second cell population.

In an embodiment, an apparatus includes a memory and a processor operatively coupled to the memory. The processor is configured to receive an indication that a user plans to generate a second cell population of a cell line based on a first cell population of the cell line. The first cell population is digitally represented by a first node in a directed tree. The processor is further configured to send, automatically in response to receiving the indication that the user plans to generate the second cell population, a signal to cause display of a default protocol associated with the cell line. The processor is further configured to receive, based on input from the user, an indication of a change to the default protocol that generates a modified protocol. The processor is further configured to generate a second node that (1) is a child node of the first node, (2) is connected to the first node via an edge in the directed tree, and (3) digitally represents the second cell population. The processor is further configured to cause, after the user has performed the modified protocol on the first cell population, data associated with the modified protocol to be stored at the edge.

In an embodiment, a non-transitory processor-readable medium stores code representing instructions to be executed by a processor. The code comprises code to cause the processor to receive an indication that a user plans to generate a second cell population of a cell line based on a first cell population of the cell line. The first cell population is digitally represented by a first node in a directed tree. The code comprises code to cause the processor to send, automatically in response to receiving the indication that the user plans to generate the second cell population, a signal to cause display of a default protocol associated with the cell line. The code comprises code to cause the processor to receive, based on input from the user, an indication that the default protocol will not be modified. The code comprises code to cause the processor to generate a second node that (1) is a child node of the first node, (2) is connected to the first node via an edge in the directed tree, and (3) digitally represents the second cell population. The code comprises code to cause the processor to cause, after the user has performed the default protocol on the first cell population, data associated with the default protocol to be stored at the edge.

BRIEF DESCRIPTION OF THE DRAWINGS

FIG. 6—A flowchart of a method to generate nodes associated with cell populations of a cell line, according to an embodiment.

FIG. 7—A flowchart of a method to store data associated with a modified protocol at an edge, according to an embodiment.

FIG. 8—A flowchart of a method to store data associated with a default protocol at an edge, according to an embodiment.

FIG. 12B—A screenshot from a protocol screen, according to an embodiment.

DETAILED DESCRIPTION

Figure 1:
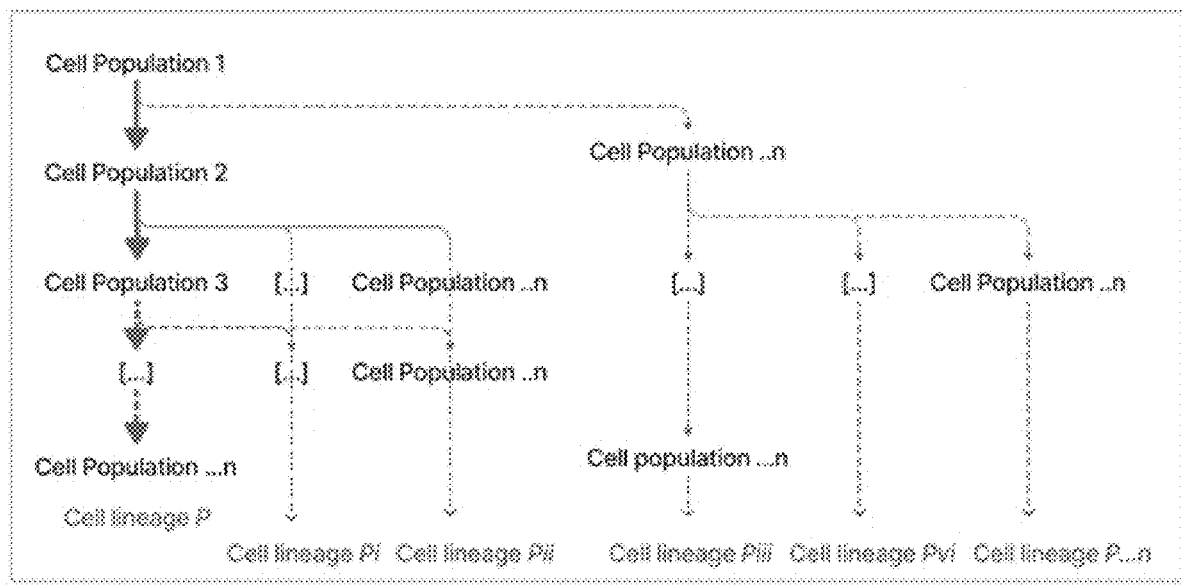
FIG. 1—A cell line tree that includes cell populations and cell lineages, according to an embodiment.

Some implementations are related to a directed tree. The directed tree, sometimes referred to herein as a "cell line tree," can store and display information associated with a cell line. The directed tree can include multiple nodes and multiple edges connecting the multiple nodes. Each node can represent a cell population of the cell line in the directed tree, and each edge going from a first node to a second node in the directed tree can be associated with data about separate observations about the cell populations at that time, separate actions performed (e.g., replaced media, initiation reprogramming treatment, etc.), and indicating a protocol that can be performed and/or has been performed to generate a cell population represented by the second node using the cell population represented by the first node.

One or more embodiments are related to:
1. A method to populate data associated with a single node of a cell line tree, and an semi-automated rapid method to capture protocols sequences performed on cell populations:
   a. A method to auto-display a protocol sequence that includes steps and key: value pairs, for each time a user performs a protocol.
   b. A method to customize pre-set protocol sequences, and set protocol sequences as default.
   C. A method that creates stored (historical) records of key: value pairs that: after completion are stored as "data" that (1) becomes part of the overall cell provenance data for a cell lineage, and (2) can be used to set a new default protocol sequence. Thus, a guideline (e.g., set of steps) for a cell population (e.g., at time t=1) can initially be proposed, and if saved for that cell population (or populations), such information can becomes part of the overall cell provenance data for a cell lineage, and/or can be used to set a new default protocol sequence.

d. A method to maintain the relationships between protocol sequences at particular time points applied to cell lineages that can be derivatives of the same cell line. i) A method to maintain the relationships between observations done at particular time points for these cell lineages after performing the protocol sequence, or inputting additional separate observations;

ii) A system to surface cell line provenance information, separating intellectual property (IP) protected or sensitive information from non-proprietary data.

A method to extract summary statistics about a cell population that is being shared, which helps the recipient to evaluate the quality of this asset. The summary statistics further help the sender to ensure proprietary data and IP-protected data are kept secure. A method to generate a custom provenance transfer report that saves time over existing approaches.

e. A method to share cell data segments in a secure way: i) Static: Filter for only those data pieces that a user wants to share, review if this data is appropriate for sharing, create, for example, a PDF or Microsoft Excel report, and send the data as part of a static report. This can be relevant to senders for ensuring that proprietary data and IP-protected data is kept secure, while still allowing senders to be able to share data so that progress in biomedical R&D can be made more efficiently. ii) Dynamic: The user can also provide access to user-selected fields with data via the system-updates to the shared fields can be followed by the recipient if the user opts for this.

f. A system that that allows the user to structure complex decision trees in the process of moving cell populations from one culture vessel to the variety of possible next destinations. A graphical representation allows the user to maintain a structured flow of information in multi-well plates or when cells are merged together.

In some implementations, techniques described herein are related to a compute device (e.g., compute device 100) configured to provide a semi-automatic supportive role to a user, such as a laboratory scientist working in a laboratory with cell tissue. In light of the described drawbacks associated with some known methods that support research scientists (e.g., inefficiency using notebooks or pdfs, lack of cell-related data relationships, etc.), some implementations described herein are related to displaying specific cell-related information in a way that allows a user to more quickly/efficiently access, analyze, and retrieve cell-related relationships between data points, thereby improving the speed of comprehensive information surfacing that supports decision making and determining course of action in the laboratory. In some implementations, techniques described herein are related to capturing data about performed activities in the laboratory that are related to cell culture, while automatically capturing the relationship to previous data, thereby improving speed and accuracy of cell-related data. Additionally, in some implementations, techniques described herein are related to determining and displaying certain (e.g., a limited set of) information (e.g., information that is not confidential, information that is ready to be shared or used, etc.), while refraining from displaying other information (e.g., information that is confidential, information that is not ready to be shared or used, etc.).

In some instances, information related to a cell line tree(s) can be extensive. As such, in some instances, the amount of information related to a cell line tree(s) may be more than what can possibly and/or reasonably be fit on a screen(s). Therefore, in some implementations, some techniques described herein can allow such information and/or key aspects of such information to be relayed to a user(s) via a screen(s) that would otherwise be smaller than desirable.

General Definitions and System Embodiment

Recapitulation of the definitions is stated in U.S. patent application Ser. No. 16/740,327, filed Jan. 10, 2022 and titled "METHOD FOR MONITORING AND MANAGEMENT OF CELL LINES USING PERIODIC LOW-COVERAGE DNA SEQUENCING DATA", the contents of which are incorporated by reference in its entirety herein.

A "cell line" is cell tissue that has been derived from a single organism (e.g., person) and can proliferate in an in vitro state. It constitutes a collection of relational "cell populations" during its in vitro time.

A "cell population" is a specific collection of cells in a culture vessel from seeding to confluence. Though the term cell population is mostly used in the context of "active cultures," a cell population (or also a group of cells) can also be frozen and stored in a cryotube, be disposed of, and/or the like.

A "cell tree" a collection of related derivative cell populations represented by nodes. All cell populations that are part of a single tree have the same germline DNA profile, and can be matched to each other via DNA analysis and matching. However, lineages derived from the original cell population may get/become manipulated (e.g., genetically, through treatment) possibly imposing small changes to the germline DNA profile. A cell tree has a single node of origin—the root node. This root node can represent the first tissue samples since extraction from an individual/organism, or it can represent a cell population that arrived in the laboratory (e.g., through purchasing, receiving from a hospital, receiving from a collaborating laboratory, receiving from a biobank, or other) that will be onward cultured in a petri-dish. For any nodes in the cell tree, following the node-edge path in reverse always leads back to the root node. A schematic to clarify the concept of a cell line tree that includes multiple cell population and cell lineages is shown in FIG. 1. In some implementations, the cell line tree is a directed tree.

"Active culture status" a cell population in a culture vessel placed in an incubator set to temperatures and environmental factors that generally support cell division (mitosis). Active culture status is different from a frozen state or a disposed state. The active culture state implies a next step is required in the near future (minutes, days, weeks). This next step can be to, for example, passage, freeze, replace media, add a treatment, dispose, genetically manipulate, analyze, or other.

"Frozen culture status" is where a group of cells is in a cryotube (or similar) stored at temperatures below −80° C. These cells do not multiply, and are kept in static state for indetermined time.

"Passaging," is the act of taking a subset of cells from a cell population and moving these to a new container (culture vessel).

Figure 9:
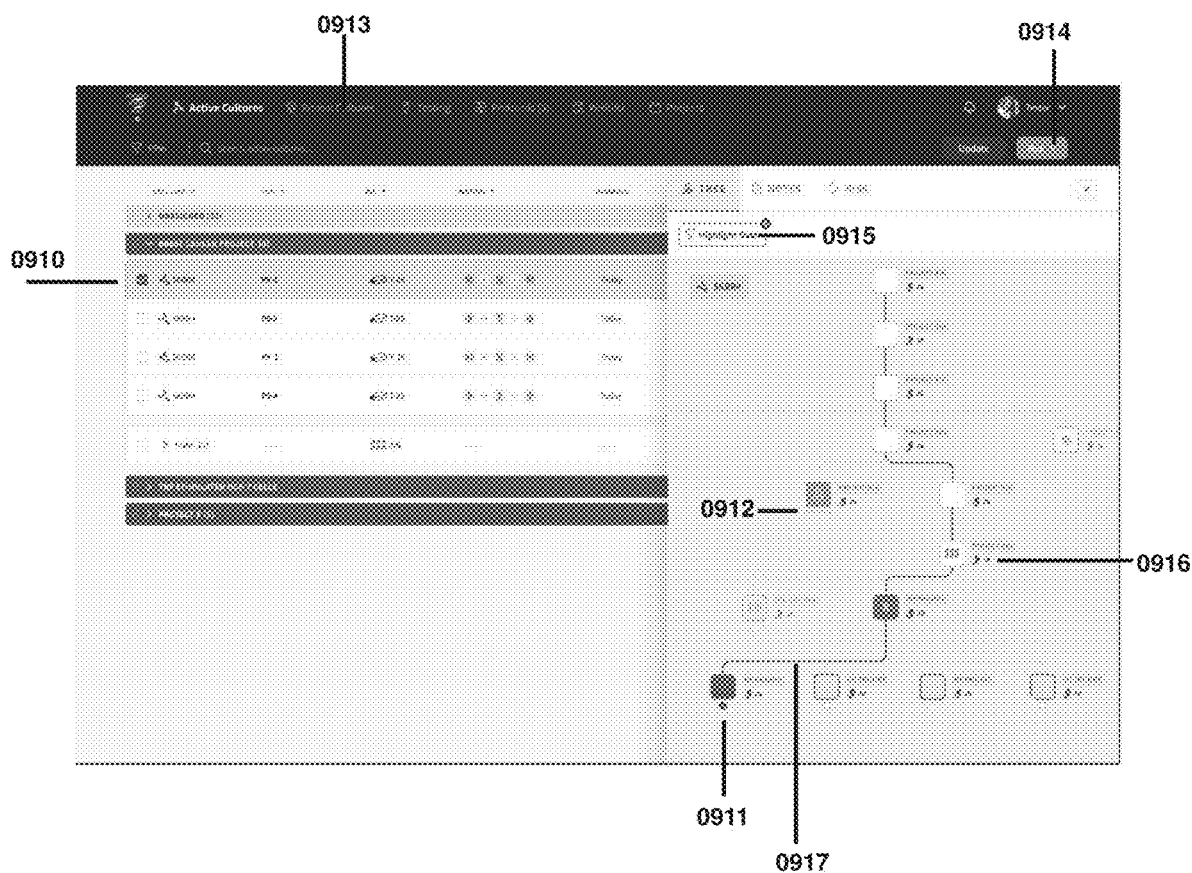
FIG. 9—A cell line tree represented in a graphical user interface (GUI), according to an embodiment.

Cell lines are composed of cell populations forming lineage paths that can trace their way back to the same original cells from the patient cell tissue sample (see, e.g., the lineage path 0917 in FIG. 9). Continuously performing passaging and/or freeze/thaw cycling results in the formation of a "cell lineage". A lineage is a single path in the cell tree from a node, following the edge-node path back to the origin node. Each act of "passaging and splitting" in two or more separate containers creates two lineages. Lineages continue upon sharing of a cell population between scientists or laboratories. The act of sharing/selling between laboratories does not discontinue a lineage in the present system, but for the laboratories who receive the cell population, they will see within the present system a new root node with key information associated (summary statistics, or a more extensive transfer report) representing the provenance of the lineage prior to owning their cell population.

An "action" can be a specific task that is done in a laboratory, a specific instruction for a single step, or an observation. Actions are often expressed as key: value pairs (there are exceptions).

Cell populations that require a single action and do not take cells out of the petri-dish is an example of an "update." An update can be an observation(s), action (e.g., add treatment), or change (e.g., media replacement). Updates can be saved regularly (e.g., daily, hourly, or more frequently) in the system as data associated with the specific selected node as a key: value pair.

A "key: value" pair: A key can be (but is not limited to being) a single word, and can be, for example, a verb or any other category of word. The value can be set to anything and can have any length; it can be structured or unstructured (for example, free text string, numerical, list of options, timer, other). A value can be a file in some variations. Sole values can be used to perform calculations.

A "node": a digital representation of a cell population that resides in a container (e.g., petri-dish, cryotube, or other). A node holds (e.g., stores) information such as data added via updates or data from protocol sequences.

An "edge": a digital representation of the relationship between two or more nodes. An edge holds information such as data added via protocols, that describes actions taken to create the new nodes.

A "user": a person who works in a laboratory with cell cultures and interacts with the present system.

Automated Capture Cell-Related Relationships, their Protocols, and Notes

In an embodiment, a system represents the journey of cells that are extracted from an individual (human, mouse, plant; or any multi-cellular organism) that accordingly are established in a petri-dish (e.g., is able to grow in an in vitro state) and kept alive. In one embodiment, the system represents the first group of cells (cell population) in a graphical representation as a first "node". A node in the system represents a cell culture vessel with a cell population within it, which are a group of cells from seeding to confluence. In vitro cell populations that are in an active state always require a next state (e.g., daily, every few days, weeks), an activity in the laboratory that involves taking a subset of cells and transferring them to a different container(s). Examples of different containers include a new petri-dish, a freezer tube, or disposing the cells. This relationship between states is captured and digitally represented using an initial node (e.g., parent node) that receives an edge (line) connected to the next node(s) (e.g., child node(s)). The number of next nodes (containers) can be infinite for a given tree. The edge can hold information about the protocol describing what the user did to get from the first node to the next node(s).

Said differently, a first cell population can be digitally represented using a first node, a second cell population generated based on the first cell population can be digitally represented using a second node, and the second node can be a child node of the first node. Steps taken to generate the second cell population from the first cell population can be digitally represented as an edge connecting the first node and the second node. Such a process can be repeated for any number of nodes and edges.

In some implementations, a system enables the user to:
i) instantly call a cell line specific protocol sequence,
ii) capture notes and make protocol alterations, and
iii) capture the relationship between this data and previous data in semi-automated way.

This reduces the number of clicks and amount of typing by the user, removing human error and saving times. For example, a user wants to "passage" a cell population from one culture vessel to two new culture vessels. According to an embodiment, the user selects the starting cell population/ node (e.g., via the list view, or via the cell graph), selects "run protocol," selects the protocol (in this example: "passage"), and goes directly to the "protocol page." The system pulls up the cell line specific protocol sequence that is set as default for "passage", and the user gets presented the protocol sequence for passaging for this specific cell line. Protocol information can be any "action" relevant to complete the goal; examples include: what media to use, supplements that this particular cell line needs according to the standard protocols (see, e.g., FIG. 10), method to dissociate cells from the petri-dish, speed at which cells should be centrifuged, type and size of destination vessel to use (flask, dish, multi-well, etc.), cell counting, microscope images that are standard to include, and/or the like. Each action is represented as a key: value pair. For example, a key: value pair could be: key=spin, value=500 rotations per minute (rpm) for 5 minutes. Values can be strings of letters, characters and numbers, or numerical. Numbers/numerical values enable direct computations. For protocols, the order in which actions are executed often matter, and are therefore presented in that order.

When no alterations are needed to the default protocol that is displayed: the user views the action prompts displayed for that default protocol, enters the number (and type of) destination vessel and confirms protocol completion once completed. Completion of a protocol trigger system updates including:
i) The captured protocol steps convert from protocol steps to data that describes the steps and values that went into going from the initial cell state to the next. The system stores this data with the specific edge and/or node.
ii) the graphical interface will automatically reflect the edge(s) and the connected nodes representing the new cell Population(s). Non-maintenance actions on cell populations are referred to as "Special Actions"—these can include genetic manipulations, (drug) treatments, genetic tests, storing a sample, etc. These can be represented with special icons/symbols.
iii) the active cell culture list view lists the updated set of nodes having active culture status (and doesn't show nodes that no longer have active culture status).

Users who do make alterations while performing the protocol actions in the laboratory, such as adding actions, changing the order of actions, changing values associated with actions, or completing a protocol, prompt the system to store this data with the specific edge and/or node associated with the alterations. Henceforth; when the user enters the action(s) changes, enters the number (and type of) destination vessel and confirms protocol completion, this data is stored in the relevant edge and/or node. Completion of this scenario triggers the system similar as above, with some differences:

i) the captured protocol steps convert from protocol steps to data that describes the steps and values used to go from the initial cell state to the next. The system stores this data with the specific edge and/or node.

ii) the graphical interface will automatically display a graphical output such as a graphical representation of the directed tree (e.g., the edge(s) and the connected nodes representing the new cell Population(s)). "Special Actions" are represented with special icons/symbols.

iii) the active cell culture list view lists the updated set of nodes having active culture status (and doesn't show the nodes that no longer have active culture status).

iv) the user is asked if they would like to save the changes as a new protocol sequence. The user can set the new protocol as a default protocol. The next time a user selects to passage this cell line, the new default protocol is displayed. All saved protocol can be retained in the system, timestamped, and user associated so that the user and/or a different user can view these previously used protocols as needed and/or set them again to default.

Cell populations that require a single action and do not take cells out of the petri-dish is an example of an "update." An update can be an observation(s), action (e.g., add treatment), or change (e.g., media replacement). Updates can be saved regularly (e.g., daily, hourly, or more frequently) in the system as data associated with the specific selected node as a key: value pair.

SYSTEM DESCRIPTION

Figure 2:
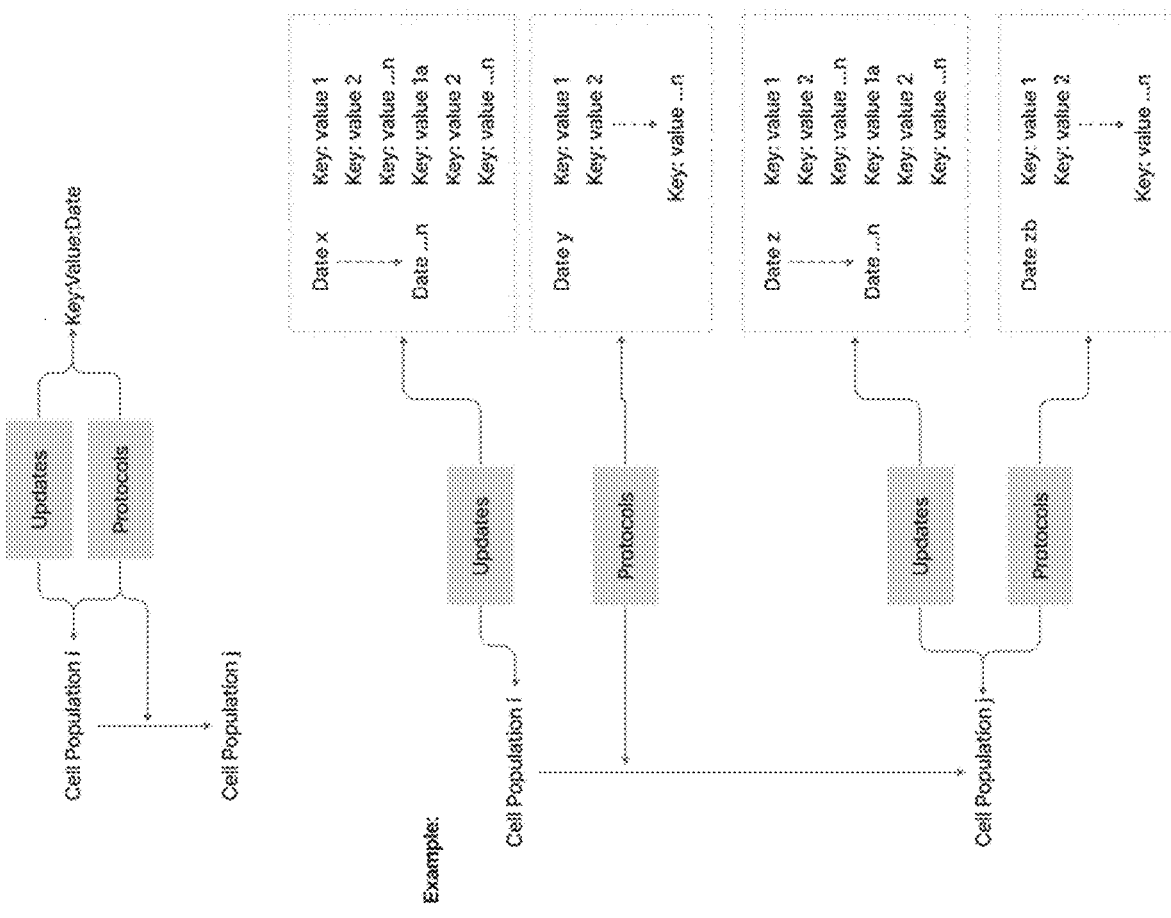
FIG. 2—Action and relationships leveraged in a system, according to an embodiment.

Some implementations are related to cell trees for cell lines, where each cell tree is associated with a single cell line and cell populations are represented in the trees as nodes. After creating the first node (i.e., the root node), all consecutive (derivative) nodes will be connected via edges. Each edge represents what was done to a cell population represented by a parent node connected to that edge to create a cell population represented by a child node connected to that edge. These relationships can also be presented to users in an easy-to-navigate graphical user interface (GUI). Following a node-edge path in reverse always leads back to the original node. Nodes can contain data that is an "update" or a "protocol". Edges can store protocol data that described how the node (cell population) got from the initial State (FIG. 2; Cell Population i) to the next state (FIG. 2; Cell Population j). The data associated with an edge can in some embodiments be displayed in a node.

Both protocols and updates are made up of key: value pairs reflecting action items. The difference between a protocol and an update is that a protocol is a sequence of key: value pairs (e.g., multiple key: value pairs) in a specific order. Updates are a single or a collection of key: value pairs in no particular order.

A single node can have multiple updates and/or protocols associated with it. These can be entered over a timespan the cells associated with that node reside in the petri-dish and are part of that specific cell population (e.g., can be hours, days, weeks, month, etc.). Stored key: value pairs can be associated by a date (and possibly time) stamp.

Figure 3:
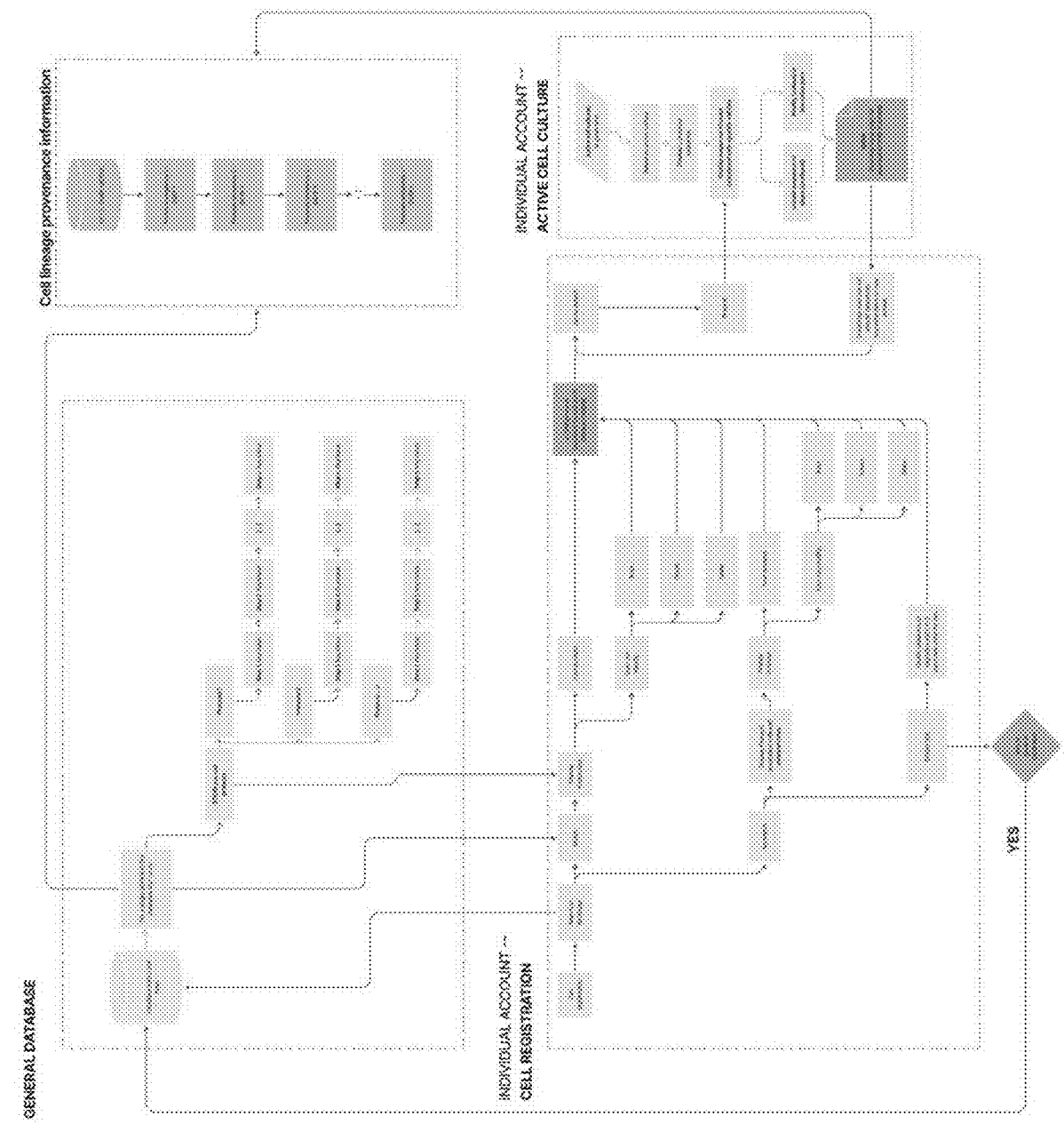
FIG. 3—A method to automate cell line & cell population specific protocols display, according to an embodiment.

In some implementations, ae system consists of four interconnected segments: i) a general database, ii) cell lineage provenance information, iii) an individual account for cell registration, and iv) an individual account for active cell culture, according to an embodiment. (FIG. 3).

Therefore, in some implementations, the system to create cell trees in real-time, frictionless and with one or more users in a laboratory setting, is as following:

1. General Database

A general database (not shown) can contain unique cell line entries (such as Hek293, MCF-7, HeLa). Here, "general database" can be composed of a preloaded cell database (e.g., FIND database) or an internal database that is created by an organization or laboratory team (e.g., by completing cell registration >new cell line).

In both cases, for each cell line in the database, global cell line information, in vitro growth specifics, and specific protocols are stored. Multiple protocols can be associated with a particular cell line (for example, a protocol for passaging, thawing, freezing, reprogramming, differentiation, etc.).

Figure 3A:
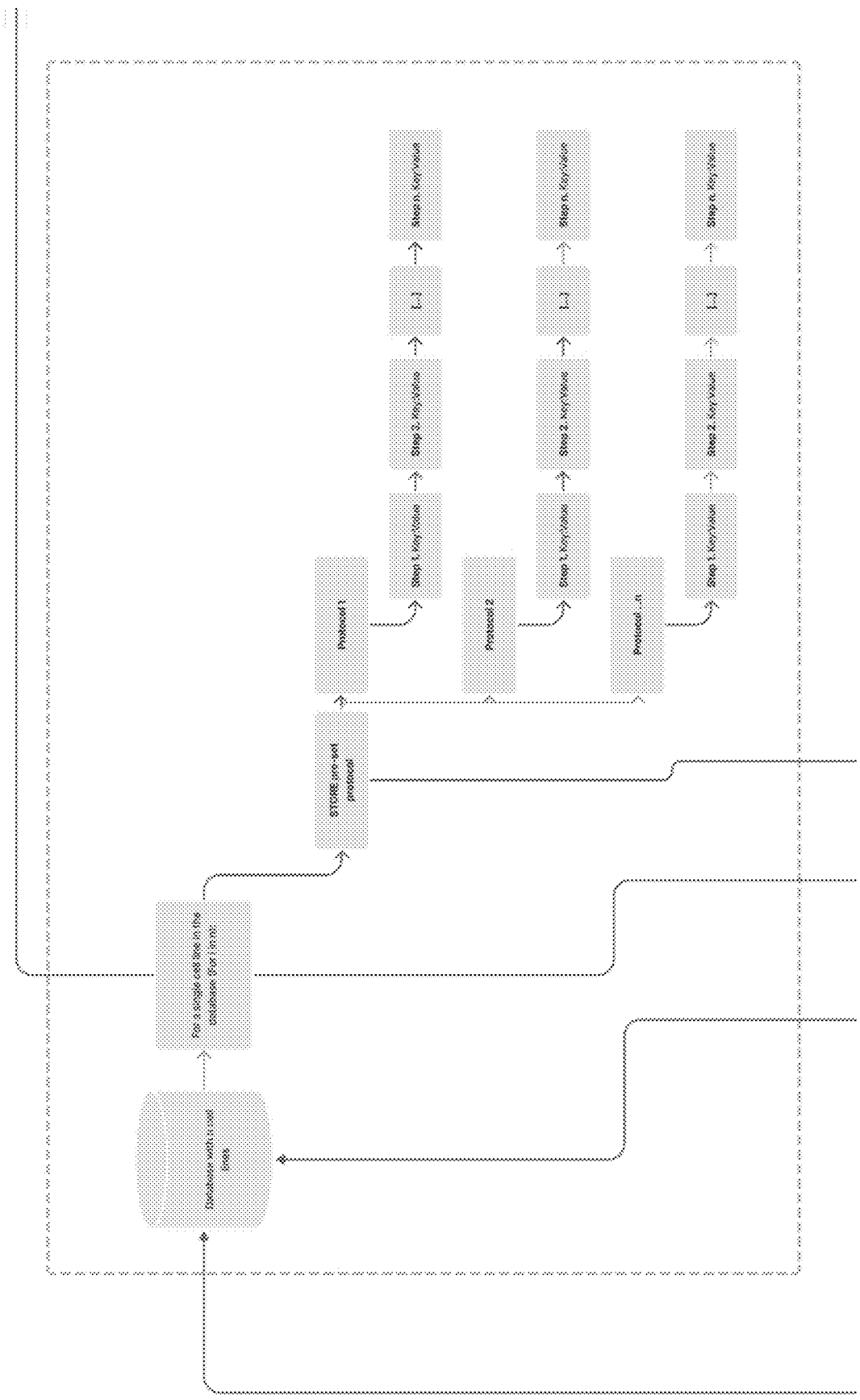
FIGS. 3A-3D show zoomed in portions of FIG. 3.

Each protocol can be a sequence of steps represented by a specific set of key: value pairs, in a particular order (FIG. 3A).

2. Individual User Account-Cell Registration

In some implementations, each individual user has their own login and account, which can be part of a group, organization, or cohort. Each user can register cell lines and maintain these as cell line owners and/or contributors.

Figure 3B:
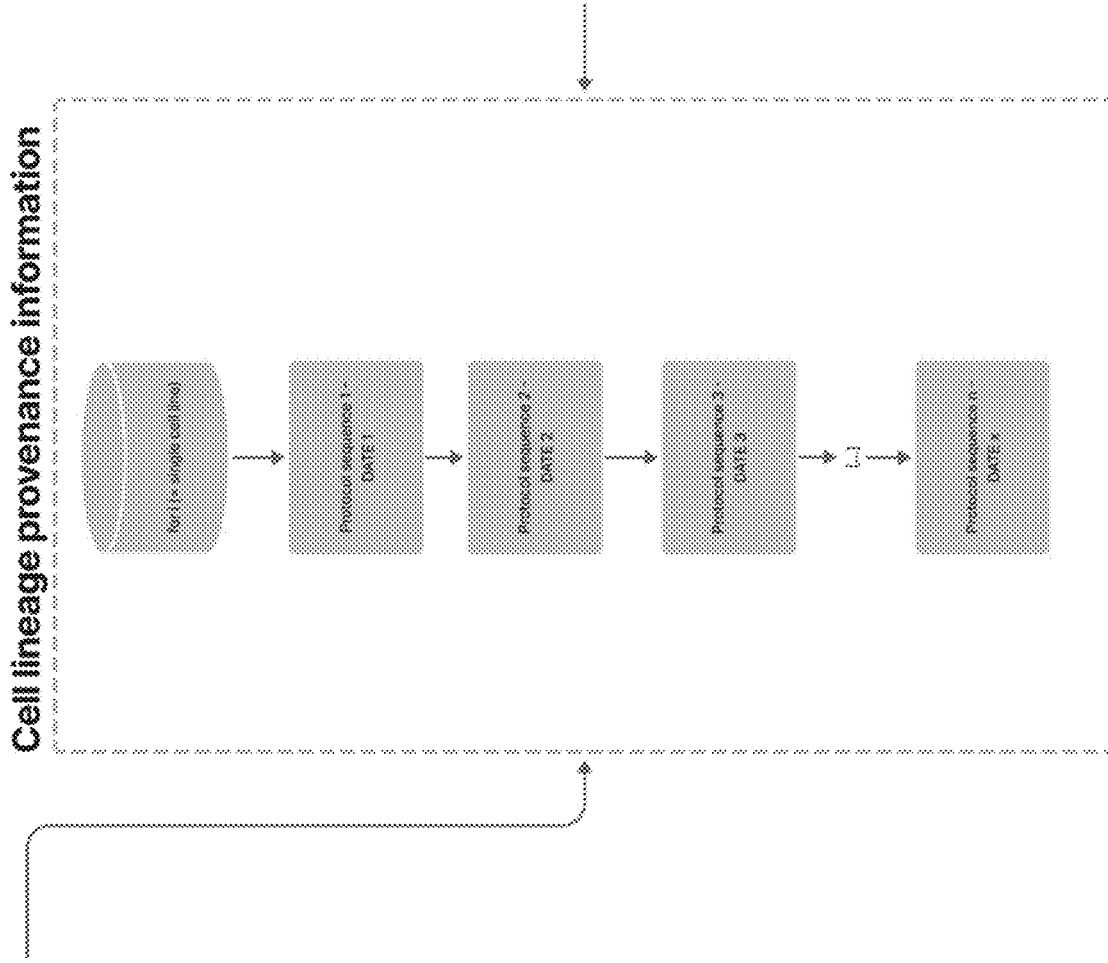
Figure 3C:
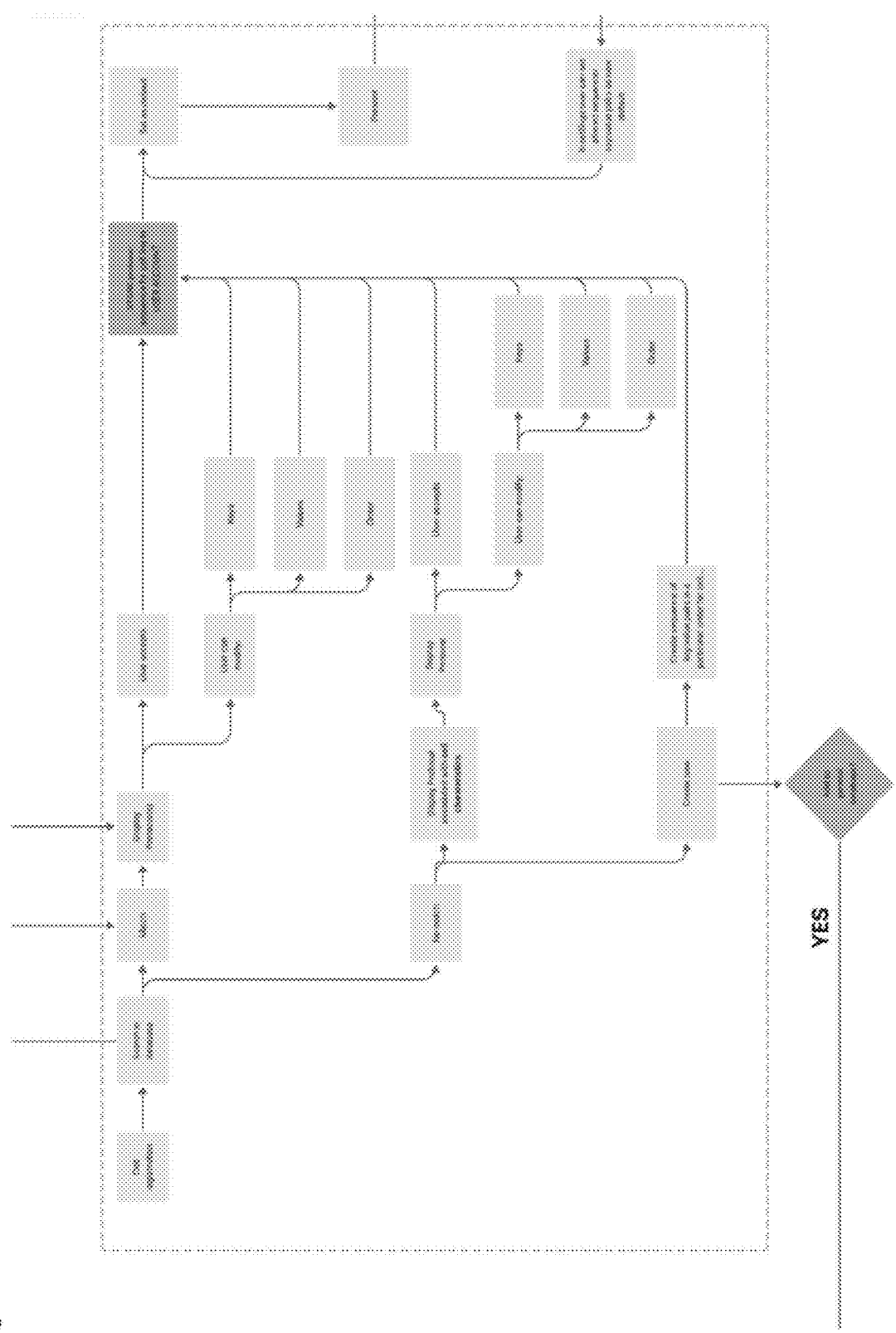

The first step of cell registration can involve searching for the cell line (e.g., by name, characteristics, or any other identifier) in the general database (via menu option "Advanced Search" for example) (FIG. 3C):

a. Match: When the search term is matched to an entry in the database, the user can choose from which database he/she would like to leverage the data. The system then presents the pre-set protocols for that cell line if they are available. For each protocol, the user/individual can evaluate if this is correct (subjective activity), or if they want to make changes (FIG. 3C). Changes can include:
   i. Changing the order of the key: value pairs,
   ii. Adding keys and values, and/or
   iii. Altering one or more values associated with keys.
Then, the user saves the altered protocol sequence, which the system can now set as the default protocol for this individual user for that particular cell line [see FIG. 3C].

b. When no match is found, the system can present protocols that are typical for specific cell characteristics (such as growing adherent, in suspension, or as a 3D culture). The user can be presented with a pre-set sequence of key: value pairs, and can modify these as needed as described above (see FIG. 3C), c. The user can also choose to create a protocol from scratch by composing a sequence of key: value pairs from an empty canvas (see FIG. 3C).

For cell lines that were not found in the general database, the newly added cell line can be stored in the general database. This way, team members (individual users who are part of the team) can leverage this data going forward. As such, the general database can be updated/transformed over time with the addition of cell lines. In some instances, the addition of cell lines to the general database can improve usefulness/completeness of the general database.

3. Individual User Account-Active Cell Cultures

Representations of active cell cultures are displayed to the user in the software system in a list and in the graphical presentation of the cell tree. These can be the last (e.g., most recent) node(s) that are added to the cell tree. Selecting an active cell culture enables the user to view information (e.g., updates, protocols, etc.), view provenance information (e.g., information associated with previous nodes in the lineage), perform an action (e.g., run a protocol, or add an update). The active culture view is a way to segment priority for the user by only displaying cell populations that need their attention.

Figure 3D:
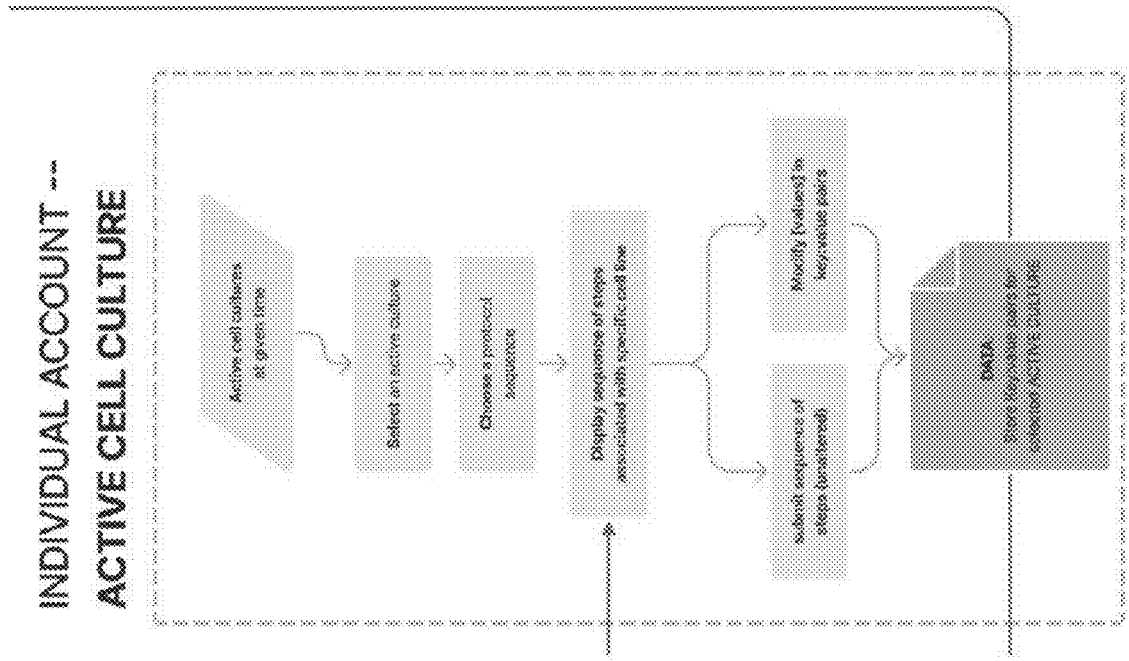

Choosing to activate a protocol prompts the system to display the protocol that is specific (e.g., default) to the selected cell line (FIG. 3D).

Possible workflows: (1) The user can read the protocol sequence, indicate the next cell state (e.g., container), and if no changes are made, complete the protocol. The sequence of key: value pairs is now stored (e.g., at the edge) as data associated with the cell population at that point in time (FIG. 3D). (2) The user can alter the values of one or more keys (e.g., change the value belonging to a key, change the order of key: value pairs, add key: value pairs, and/or save this information. The sequence of key: value pairs is now stored as data associated with the cell population at that point in time.

Set as new default protocol: The user can select this altered sequence of key: value pairs and set it as default for that protocol title for this cell line (FIG. 3). The user can always revert a protocol back to the original state, according to an embodiment.

An advantage of allowing new defaults is that systematic alterations do not have to be typed in again each time the user wants to perform the altered sequence of steps. Cells can evolve over time (intentionally or unintentionally) (see, e.g., Zaaijer, S., Groen, S. C., Sanjana, N. E. (2021). Tracking Cell Lineages To Improve Research Reproducibility. Nat Biotechnol, 6 (39), 666-670. https://doi.org/10.1038/s41587-021-00928-1; which is incorporated herein by reference), and alterations to protocols may be required.

4. Cell Lineage Provenance Information

For a specific cell line tree, each cell population may—or may not—have a unique sequence of key: value pairs stored. Collectively, the sequence of all dated (and optionally timestamped) steps (including protocol steps and updates) for a cell lineage that is part of a cell line tree makes up the "cell provenance" information (FIG. 3B).

One or More Embodiments Include

Production of records of alterations/permutations to these displayed values, that: 1) are now stored as 'data'—this data becomes part of the overall cell provenance data for a cell lineage, and 2) can be used to set a new default protocol sequence.

Using these protocol key: value sequences, update key: values associated with each node, and compare them to their related node as connected via edges. This can be a way to understand how variations contribute to phenotype changes in cell lines/cell populations. For example, isolating/filtering for two or more keys and displaying values for all cell populations in a lineage (or multiple lineages) over time, to perform causation analysis for—for example—understanding how specific environmental factors affect cell behavior (changes in cell's morphology, viability, cell doubling, molecular pathways, etc.).

Infer correlations between protocol key: value sequences to update key: values associated with each node and compare them to their related node as connected via edges.

Leveraging these structured data sets as training data for artificial intelligence or machine learning algorithms for predictive modelling how certain actions (key: value pairs) affect cell growth, viability or morphology.

Controlled Data Sharing

Figure 4:
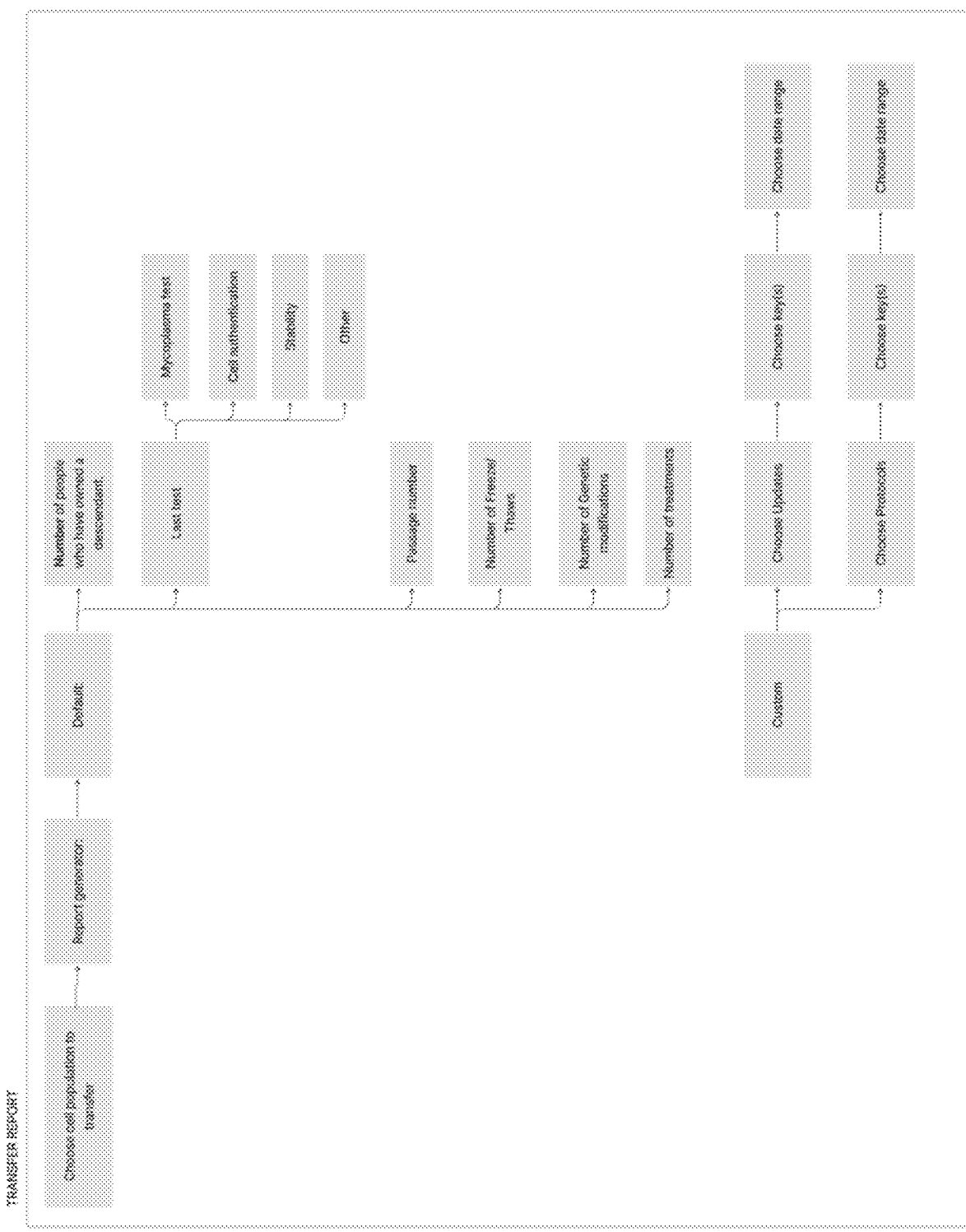
FIG. 4—A method for controlled data sharing and generating a cell provenance report, according to an embodiment.

Some implementations are related to generating a rapid cell provenance report that facilitates controlled data sharing (FIG. 4).

Transfer Provenance Report

For a cell population that is desired by another party and/or needs to be transferred (as active or frozen culture) the user can generate a transfer provenance report (also referred to as provenance report) for the associated cell lineage (FIG. 3B-within dashed box labelled "Cell lineage provenance information", and FIG. 4).

1. Default Setting for the Transfer Provenance Report

A default report can be generated for a cell population of interest (e.g., in Microsoft Excel, PDF, or via the system). The user can select to include global cell line information (e.g., organism, tissue type, disease, age, sex, ancestry) and/or the source(s) of this information (e.g., large biobank, data repository, user-entered, other)

For the cell lineage related to the cell population the report will output at least one of:
 1. Number of previous owners the cell lineage had;
 2. Passage number (as counted by the system);
 3. Number of freeze/thaw cycles performed;
 4. Last tests performed (mycoplasma, authentication, stability)—not the data.
 5. Number of genetic modifications made (attempts or successes); or
 6. Number of treatments received.

The values are extracted from the provenance information (as described above) based on keys or protocol names.

The standard output can be displayed as aggregated, meaning the counts of key occurrences for cell populations that preceded the selected cell population in the lineage are summed up and reported. The statistics based on the aggregated data can be displayed and presented to the user (for example: Previous Owners: 5, Mycoplasma Tested: 5 times, Frozen: 4 times, Genetic Manipulations: 2). The display of the aggregated data statistics ensures user privacy and data security; perhaps the user is willing to share some indications but not the exact dates and the names of the owners as this is considered privileged/private/intellectual property information. The aggregated provenance information associated with the cell population on display can be transformed into, for example, a PDF or Microsoft Excel file (static form, a file can be sent by email or equal), or can be sent via the system to the appropriate recipient(s) (dynamic; updates are pushed to recipient in real-time).

2. Custom Transfer Report Generation:

The user can choose to create a customized report where they can choose to share only certain values based on certain keys. A report can be generated in which the user selects to include specific historical information such as: Category (Protocol type/Update), specific keys within category, and time period.

For example, to create a report, a user can choose in a menu: "updates," then: "confluency," "media change," and "microscope image" between Jan01-2021-March01-2021. In this case, protocols will be skipped, and only keys that are in updates will be displayed.

Another example: In "protocols", a user can choose "passages," then: "Flask type," "Flask size," "confluency," and "seeding" between Jan01-2021-March01-2021. Now only key: value data entities that are in the protocol passage are displayed over the indicated timeframe for the lineage preceding the selected cell population.

For protocol sequences specifically, the user can choose to display a default protocol key: value sequence for that cell line, or present data over a particular (e.g., predetermined) time period (which can include alterations if these were made during execution).

Embodiments Include

Extraction of summary statistics about a cell population that is being shared, which helps the recipient to evaluate the quality of the cell population. This is similar to CarFaxIM reports for second hand cars. The summary statistics further help the sender to ensure proprietary data and IP-protected data are kept secure.

The generation of a quick custom transfer report leads to time savings over existing approaches when protocols are being shared between labs (or when a manuscript is being written).

The custom transfer report offers a mechanism to pull up and share only those data elements that are key for a transaction (for example, a user may perhaps only want to share information on genetic modifications and selection markers, but not on every observation over the past five years).

The custom transfer report is a vehicle to share data segments in a secure way:
Filter for only those data pieces that a user wants to share, review if this data is appropriate for sharing, create e.g., a PDF or Microsoft Excel report, and send the data as part of a static report. This is relevant to senders for ensuring that proprietary data and IP-protected data is kept secure, while still allowing senders to be able to share data so that progress in biomedical R&D can be made more efficiently.

The user can also provide access to user-selected fields with data via the system-updates to the shared fields can be followed by the recipient if the user opts for this.

Hardware

Figure 5:
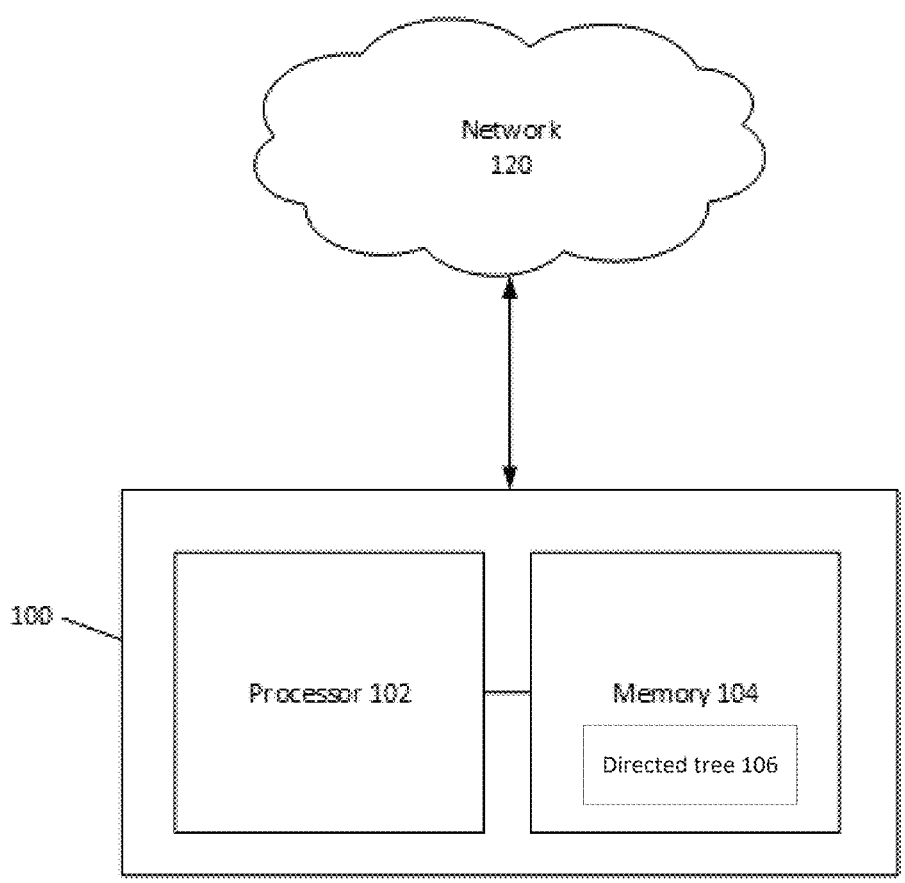
FIG. 5—A block diagram for hardware that can perform one or techniques described herein, according to an embodiment.

In some implementations, the techniques described herein can be applied across one or more compute devices (e.g., a single compute device and/or multiple compute devices). FIG. 5 shows an example of a compute device 100 that can implement one or more techniques described herein.

Compute device 100 can be communicably coupled to a network 120, and can include a processor 102 and memory 104 operatively coupled to one another (e.g., via system bus). The compute device 100 could be, for example, a server, a computer, a mobile device, and/or the like.

Processor 102 can be, for example, a hardware based integrated circuit (IC) or any other suitable processing device configured to run or execute a set of instructions or a set of codes. For example, the processor 102 can include a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), a graphics processing unit (GPU), a neural network processor (NNP), and/or the like. In some instances, the processor 102 can be operatively coupled to the memory 104 through a system bus (for example, address bus, data bus, and/or control bus, not shown).

The memory 104 can be, for example, a memory buffer, a random access memory (RAM), a read-only memory (ROM), a hard drive, a flash drive, a secure digital (SD) memory card, a compact disk (CD), an external hard drive, an erasable programmable read-only memory (EPROM), an embedded multi-time programmable (MTP) memory, an embedded multi-media card (eMMC), a universal flash storage (UFS) device, and/or the like. The memory 104 can store data (for processing by the processor 102), and/or codes representing instruction to be processed by the processor 102.

The memory 104 can include (e.g., store) a directed tree 106. The directed tree 106 can be associated with a single cell line and represent a cell line tree. The directed tree 106 can include any number of nodes and edges. Each node can represent a cell population. Nodes can be connected to other nodes via edges. Each edge can indicate what was done to the cell population associated with the parent node of that edge to generate the cell population associated with the child node of that edge. For example, the root node of the directed tree 106 can digitally represent a first cell population from an organism. A child node of the root node can digitally represent a second cell population that was generated by performing a protocol on the first cell population, and the child node and parent node can be connected together via an edge indicating (e.g., storing) data associated with the protocol that was performed.

The directed tree 106 can change over time. For example, a user can repeatedly add additional nodes and edges to the directed tree 106, those additions representing actual actions performed (e.g., in a laboratory setting by a scientist). Although only one directed tree is shown in FIG. 5, any number of directed trees can be stored in memory 104, each directed tree associated with a single cell line and representing a cell line tree.

In some implementations, a user wants to perform a protocol on a first cell population (e.g., having active culture status, having frozen culture status, etc.) to generate a second cell population. In such a case, a default protocol associated with the cell line can be shown to the user. In some implementations, the user does not modify the default protocol; said differently, the user follows the default protocol to generate the second cell population from the first cell population. In such a case, after the user has performed the default protocol, data associated with the default protocol becomes associated with an edge connecting a first node in the directed tree 106 digitally representing the first cell population to a second node in the directed tree 106 digitally representing the second cell population. In some implementations, the user does modify the default protocol; said differently, the user follows a modified protocol to generate the second cell population from the first cell population. In such a case, after the user has performed the modified protocol, data associated with the modified protocol becomes associated with the edge connecting the first node to the second node. Further, in some implementations, the modified protocol becomes set as the new default protocol so that a subsequent request to perform a protocol based on the directed tree 106 will automatically cause the modified protocol to be shown.

In some implementations, the directed tree 106 can be used with an AI model to generate an output predicting behavior of the cell line. For example, data associated with one or more nodes and/or edges of the directed tree 106 can be input into the AI model. The system generates labelled cell-data data frames that can be leveraged in an AI, supervised learning approach (for example, with neural network algorithms) where the model is trained to predict cell change (e.g., genetic stability, morphology, viability, cell doubling fitness, expression profiles, compound production, etc.) based on protocol choices made or to be made by users in the laboratory. Critical attributes are capturing the protocol data, and the updated data (e.g., cell observations over time). Given a gap in robust knowledge about effects of decisions in the laboratory on cell behavior, the data can be leveraged for research purposes in unsupervised AI learning methods to find hidden patterns.

In some implementations, a report can be generated based on the directed tree 106. The report can include data associated with the directed tree 106, such as the number of nodes, protocols performed, and/or the like. In some implementations, the report can be generated while omitting certain information that has been indicated (e.g., by the user) as confidential. For example, the user may indicate a word, phrase, key, value, author, date range, time range, and/or the like that is used to filter out that information in the report. In some implementations, the report indicates cell provenance information (e.g., transfer provenance report). In some implementations, the report is a transfer report, such as a custom transfer report as previously discussed.

In some implementations, cell provenance information associated with the directed tree 106 can be generated. The cell provenance information can be generated based on, for example, the nodes and/or edges of the directed tree 106. The cell provenance information can be generated based on any number of nodes and/or edges, such as multiple nodes and multiple nodes, a single node and multiple edges, and/or the like.

In some implementations, each node from the directed tree 106 that has a predetermined status (e.g., active culture status, frozen culture status, etc.) is associated with a default protocol in the sense that the default protocol is automatically displayed to a user that wants to record a protocol using the directed tree 106 (regardless of if those nodes are part of a different lineage or same lineage). The user has the option to change the default protocol, but initially, the default protocol is shown.

In some implementations, updates can be stored at nodes of the directed tree 106. The updates can be, for example, observations or actions. The updates can be, for example, observations or actions for a cell population collected by a user (e.g., scientist) after the cell population has been generated. Updates are different from protocols.

Although not shown in FIG. 5, the compute device 100 can include other components, such peripheral devices. The peripheral devices could include input devices (e.g., mouse, keyboard, microphone, etc.) and/or output devices (display, speakers, etc.). In some implementations, the compute device 100 includes a display with a limited screen size (e.g., less than 20 inches, less than 12 inches, less than 10 inches, less than 8 inches, less than 6 inches, and/or the like).

Although FIG. 5 shows only a single compute device, in some implementations, any number of compute devices can be used. Any of the techniques described herein can be performed across any number of compute devices. For example, a first compute device can perform a first step, a second compute device can perform a second step, and a third compute device can perform a third step. Multiple compute devices can communicate via the network 120.

Methods

FIG. 6 shows a flowchart of a method 600 to generate nodes associated with cell populations of a cell line, according to an embodiment. In some implementations, method 600 is performed by a processor (e.g., processor 102).

At 602, a first node of a directed tree (e.g., directed tree 106) is generated. The first node digitally represents a first cell population of a cell line. At 604, an indication from a user (e.g., scientist, technician, etc.) of a protocol to be performed on the first cell population that will generate a second cell population of the cell line is received. At 606, a second node of the directed tree is generated. The second node is a child node of the first node. The second node digitally represents the second cell population. The first node is connected to the second node in the directed tree via an edge. In some implementations, 606 is performed automatically (e.g., without human intervention) in response to completing 604. At 608, data is caused to be stored at the edge after the user has performed the protocol on the first cell population to generate the second cell population. The data is a transformation of the protocol used to generate the second cell population.

In some implementations of method 600, receiving the indication from the user of the protocol includes sending a signal (e.g., electronic signal) to cause display of a default protocol associated with the cell line and receiving an indication of a change to the default protocol by the user, the change to the default protocol defining the protocol.

In some implementations of method 600, receiving the indication from the user of the protocol includes sending a signal (e.g., electronic signal) to cause display of a default protocol associated with the cell line and receiving an indication of no change to the default protocol by the user, the default protocol being the protocol after receiving the indication of no change to the default protocol.

In some implementations of method 600, the protocol is a first protocol and method 600 further includes causing the first protocol to be a default protocol for the cell line after the user has performed the first protocol. An indication is received from the user that a second protocol is to be performed on at least one of the first cell population or the second cell population. A signal (e.g., electronic signal) is sent, automatically in response to receiving the indication that the second protocol is to be performed, to cause display of the default protocol.

In some implementations of method 600, the protocol includes a sequenced set of key: value pairs.

Some implementations of method 600 further include causing data associated with the first node, the second node, and the edge to be provided to an artificial intelligence (AI) model configured to generate an output predicting cell line behavior.

In some implementations of method 600, the first cell population has active culture status when the indication from the user of the protocol to be performed on the first cell population is received.

In some implementations of method 600, the first cell population has frozen culture status when the indication from the user of the protocol to be performed on the first cell population is received.

Some implementations of method 600 further include receiving an indication of information included in at least one of the first node, the second node, or the edge, that is to remain confidential and generating a report that summarizes information included in the at least one of the first node, the second node, or the edge and that does not include the information that is to remain confidential.

In some implementations of method 600, the protocol is a first protocol and the edge is a first edge. Method 600 further includes receiving an indication from the user of a second protocol to be performed on the second cell population that will generate a third cell population of the cell line. A third node of the directed tree is generated that digitally represents the third cell population and that is a child node of the second node. The directed tree includes a second edge that digitally represents a connection between the second node and the third node. After the user has performed the protocol on the second cell population to generate the third cell population, data associated with the second protocol is caused to be stored at the second edge. A request for cell provenance information is received. The cell provenance information is generated (e.g., automatically and without human intervention) based on the data associated with the first protocol at the first edge and the data associated with the second protocol at the second edge.

In some implementations of method 600, the protocol is a first protocol and the edge is a first edge. Method 600 further includes receiving an indication from the user of a second protocol to be performed on the second cell population that will generate a third cell population of the cell line. A third node of the directed tree is generated that digitally represents the third cell population and that is a child node of the second node. The directed tree includes a second edge that digitally represents a connection between the second node and the third node. After the user has performed the protocol on the second cell population to generate the third cell population, data associated with the second protocol is caused to be stored at the second edge. A request for cell provenance information is received. The cell provenance information is generated (e.g., automatically and without human intervention) based on the data associated with the first node, the first protocol at the first edge, the second node, the data associated with the second protocol at the second edge, and the third node.

In some implementations of method 600, the protocol is a first protocol and the edge is a first edge. Method 600 further includes receiving an indication from the user of a second protocol to be performed on the second cell population that will generate a third cell population of the cell line. A third node of the directed tree is generated that digitally represents the third cell population and that is a child node of the second node. The directed tree includes a second edge that digitally represents a connection between the second node and the third node. After the user has performed the protocol on the second cell population to generate the third cell population, data associated with the second protocol is caused to be stored at the second edge. A request for cell provenance information is received. The cell provenance information is generated based on the data associated with the first node, the first protocol at the first edge, the second node, the data associated with the second protocol at the second edge, and the third node. An indication of information associated with at least one of the first node, the second node, the third node, the first edge or the second edge, that is to remain confidential is received. A report that summarizes information included in the at least one of the first node, the second node, the third node, the first edge or the second edge and that does not include the information that is to remain confidential is generated.

FIG. 7 shows a flowchart of a method 700 to store data associated with a modified protocol at an edge, according to an embodiment. In some implementations, method 700 is performed by a processor (e.g., processor 102).

At 702, an indication that a user plans to generate a second cell population of a cell line based on a first cell population of the cell line is received. The first cell population is digitally represented by a first node in a directed tree (e.g., directed tree 106). At 704, a signal to cause display of a default protocol associated with the cell line is sent automatically in response to receiving the indication that the user plans to generate the second cell population at 702. In some implementations, 704 is performed automatically (e.g., without human intervention) in response to completing 702. At 706, an indication of a change to the default protocol that generates a modified protocol is received based on input from the user. At 708, a second node is generated that (1) is a child node of the first node, (2) is connected to the first node via an edge in the directed tree, and (3) digitally represents the second cell population. At 710, data associated with the modified protocol is caused to be stored at the edge after the user has performed the modified protocol on the first cell population.

Some implementations of method 700 further include receiving, after storing the data associated with the modified protocol at the edge at 710, an indication that the user plans to generate a third cell population of the cell line. Automatically (e.g., without human intervention) in response to receiving the indication that the user plans to generate the third cell population, a signal to cause display of the modified protocol is sent (e.g., to a display of a computer device like compute device 100 and/or a compute device not shown in FIGURE. 5).

In some implementations of method 700, the edge is a first edge and method 700 further includes receiving an indication from the user of a protocol to be performed on the first cell population that will generate a third cell population of the cell line. A third node is generated that (1) is a child node of the first node, (2) is connected to the first node via a second edge in the directed tree, and (3) digitally represents the third cell population. After the user has performed the protocol on the first cell population to generate the third cell population, data associated with the protocol is caused to be stored at the second edge.

In some implementations, the edge is a first edge and method 700 further includes receiving an indication from the user of a protocol to be performed on the second cell population that will generate a third cell population of the cell line. A third node is generated that (1) is a child node of the second node, (2) is connected to the second node via a second edge of the directed tree, and (3) digitally represents the third cell population. After the user has performed the protocol on the first cell population to generate the third cell population, data associated with the protocol is caused to be stored at the second edge.

Some implementations of method 700 further include causing data associated with the first node, the second node, and the edge to be provided to an artificial intelligence (AI) model configured to generate an output predicting how protocol steps and modifications can affect risks of cell error.

In some implementations of method 700, the first cell population has one of active culture status or frozen culture status.

FIG. 8 shows a flowchart of a method 800 to store data associated with a default protocol at an edge, according to an embodiment. In some implementations, method 800 is performed by a processor (e.g., processor 102).

At 802, an indication that a user plans to generate a second cell population of a cell line based on a first cell population of the cell line is received. The first cell population is digitally represented by a first node in a directed tree (e.g., directed tree 106). At 804, a signal to cause display of a default protocol associated with the cell line is sent automatically (e.g., without human intervention) in response to receiving the indication that the user plans to generate the second cell population at 802. At 806, an indication that the default protocol will not be modified is received based on input from the user. At 808, a second node is generated that (1) is a child node of the first node, (2) is connected to the first node via an edge in the directed tree, and (3) digitally represents the second cell population. At 810, after the user has performed the default protocol on the first cell population, data associated with the default protocol is caused to be stored at the edge.

Some implementations of method 800 further include receiving an indication that the user plans to generate a third cell population of the cell line based on one of the first cell population or the second cell population. Automatically (e.g., without human intervention) and in response to receiving the indication that the user plans to generate the third cell population, a signal to cause display of the default protocol is sent.

Some implementations of method 800 further include generating cell provenance information based on the data associated with the default protocol at the edge and less structured data stored in the nodes.

In some implementations of method 800, the protocol and the modified protocol includes a sequenced set of actions.

Deployment Methods

An example of an output that can be displayed via a graphical user interface (GUI) according to an embodiment is depicted in FIG. 9. The cell line tree is embodied in the system as follows:

1 In the cell line "tree" the collection of nodes representing cell populations, and their connecting edges indicating their inheritance relationships are displayed (e.g., in a side-panel or in a full screen).
2. The list of all 'active cell cultures' is displayed in a panel (FIG. 9, 0910). In this list all culture vessels that are currently in the incubator are displayed. Clicking a node, selects the corresponding row in the list, and vice versa. The active cultures are the last entered node(s) in the tree (FIG. 9, 0911).
   a. Alternate states of the outer most nodes of the tree: Terminated cultures, which have been abandoned, destroyed, or thrown away and frozen cultures, which are visualized with a specific icon (FIG. 9, 0912). Specific information on where these cultures are stored (for example, in a box or freezer) can be retrieved in the tab "Frozen cultures." (FIG. 9, 0913)

For a cell line (see definition above), general information can be displayed in the top of a cell tree embodiment (not shown). General cell information is also referred to as "global cell information" and includes information like tissue type, age, cell characteristics, genetic ancestral background, etc.

Actions can be initiated by selecting nodes representing active cell cultures in the tree (FIG. 9, 0911) or from the list view (FIG. 9, 0910), and indicating the start of an action such as adding an update (e.g., an observation to the cells, or a media change) or a protocol (e.g., passage, freeze, reprogramming, differentiation, etc.) FIG. 9, 0914.

Within the tree, the user can "filter-highlight" for specific keys (example of such embodiment is in FIG. 9, 0915). Cell populations used in specific projects can be viewed, and/or owners of specific cell populations or lineage branches can be highlighted in the tree (example of such embodiment is in FIG. 9, 0916). The system can allow selection of numerous keys stored in the platform.

FIG. 9, 0911 and follow dark blue line 0917, shows a cell lineage in the cell line tree, according to an embodiment. A lineage in this system is defined as a sequence of nodes connected back to the origin node (i.e., root node) via one or more edges.

Figure 10:
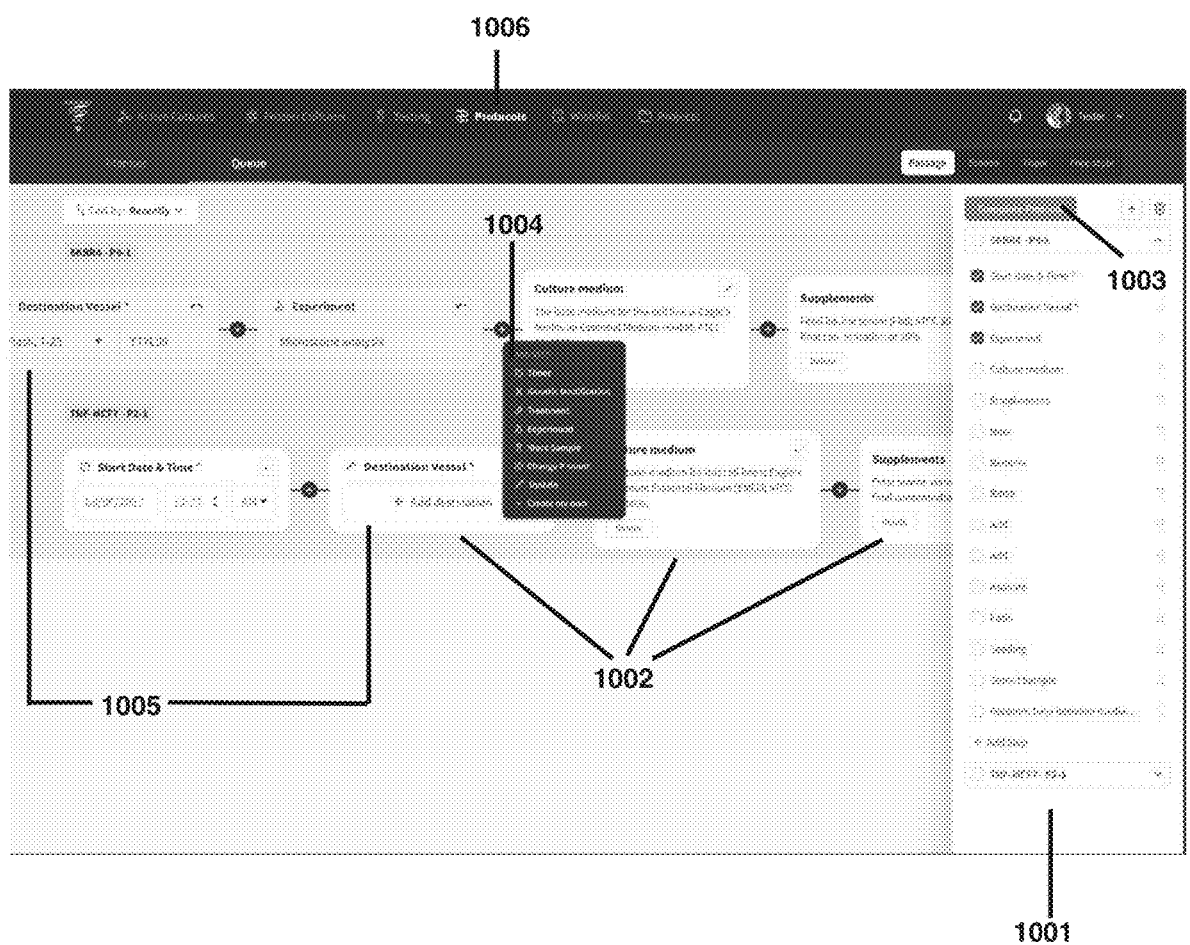
FIG. 10—An interface related to key-order and/or key: value pairs, according to an embodiment.

FIG. 10 shows an GUI related to key-order and/or key: value pairs, according to an embodiment.

The key-order of the protocol sequence is listed on a side panel of FIG. 10 (FIG. 10-1001). When in a specific protocol label (for example "passaging")—the user can select single or multiple active cell culture (here: HEK293-P2). The key: value pairs show up in connected action blocks (FIG. 10-1002). In each action block, the header states the key, while the body allows the user to view and/or edit the value. Users can execute the protocol sequence as listed and click complete (FIG. 10-1003).

User can edit blocks, add blocks (key: value pairs) (FIGS. 10-1004), remove blocks, etc.—once the user selects (e.g., clicks) "Complete Protocol," (FIGS. 10-1003) the data will be associated with this particular cell population (a group of cells at a specific timeframe).

Figure 12A:
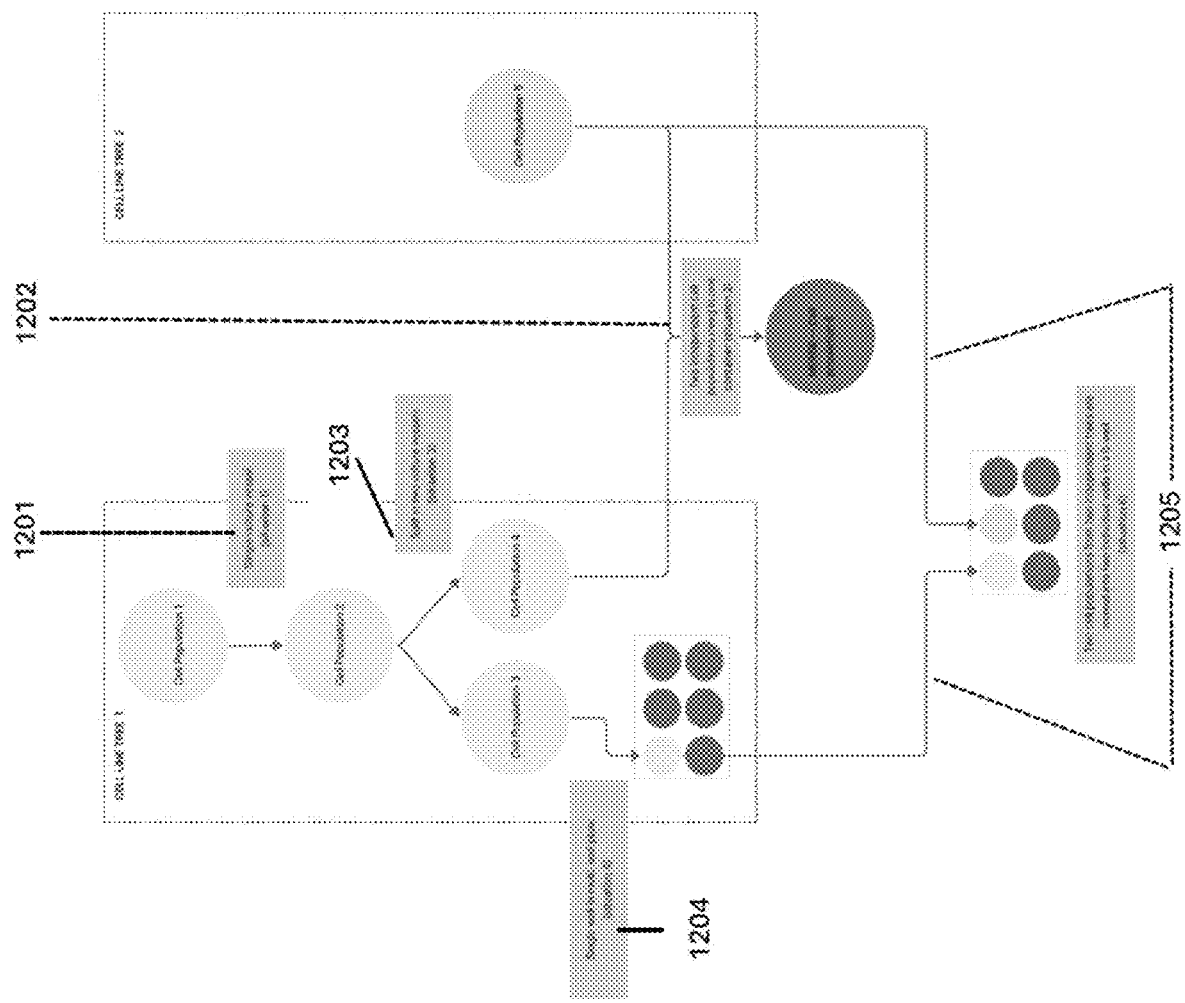
FIG. 12A—A schematic showing a method to display moving and merging cells between types of culture vessels, according to an embodiment.

In some implementations, there are alternate blocks that are not strict key: value pairs, including the destination vessel block (here (FIG. 10-1005), further explained in FIG. 12A), or the timer block for timers that can take e.g., 1 or 2 days (for freezing cells, where they stay at −80° C. for a few days and then moved to the liquid nitrogen).

To find active protocols the user can visit "Protocol" tab [FIG. 10-1006].

The user can highlight key elements in the cell line tree.

What is visible versus what is not visible in the cell line tree: In some implementations, the entire tree created by a team or organization is shown graphically (but not to users outside that team or organization). Within an organization, individual accounts can have permission settings: to allow access or block access and work in private (similar to Google Sheets™, where you can allow edit rights, viewer rights, or no access).

For users that choose to block access to their cell related data from the rest of the team that are part of the account: Nodes are created show up in the cell line tree, but are locked.

The information that is being displayed for those nodes to the rest of the team can be one or more of the following:
- The nodes in the graph generated while a cell lineage was maintained by the owner appear with a lock symbol;
- The owner of each node is displayed when the team filters for "cell population owners";
- The cell populations that are stored as frozen cultures and the number of vials available;
- If samples are stored for a specific "locked" cell population (e.g., for cell pellet, DNA, RNA, or protein);
- The locked nodes will be covered in the output of the risk analyses FINDCell performs (these analyses output results regarding cell quality metrics, including Mycoplasma infection, cell authenticity, genetic stability), and will receive risk assessments via FIND Cell's Risk simulation. However, the data associated with the locked nodes will not be part of the input data for the risk analyses or risk simulations (only the result "correctly authenticated," "Mycoplasma negative," and so on, so that data privacy for these locked nodes is guaranteed).

In this way, the user can see desired and/or essential information about a cell population's provenance-more information can be requested by asking viewing permission to the owner(s) of cell populations of interest with locked nodes (either in person, or via the system).

Example Embodiment of Filters (not Showing all)

Figure 11:
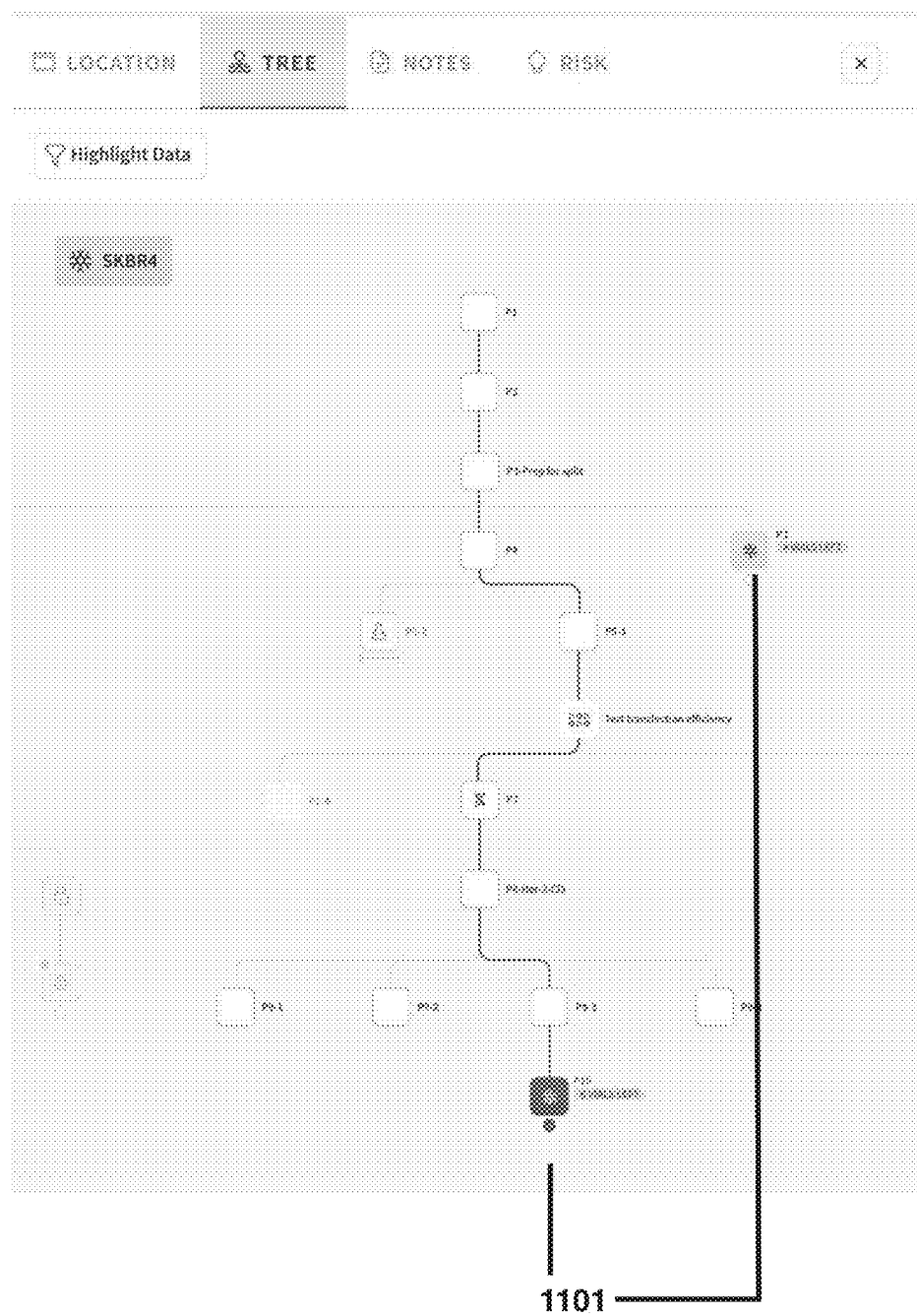
FIG. 11—A schematic showing an example of vials in frozen stock that are highlighted, according to an embodiment.

For a cell line tree, a user can select filter category. For example, the user can filter the tree based on projects and/or owners (FIGS. 9, 0915 and 0916). The project names show up as well as the names of the project owners. For locked cell populations (nodes), the owner shows up, but not the project name. Keys can be selected, and key: value data can be displayed to in the graphical tree. Another example is filtering to highlight the number of vials in frozen stock (see, e.g., FIGS. 11-1101).

FIG. 12A shows a flowchart of a method to display & track moving and merging cells between types of culture vessels, according to an embodiment.

In the process of cell maintenance and experimentation, cells are moved from one culture vessel to the next. There are a number of options for culture vessels, including flasks and dishes of various sizes. Plates may form a separate category, as these have separate compartments. Individual compartments can hold independent cell populations (either from the same cell line or from different cell lines). Plates are also referred to as multi-well plates, and include e.g., 6-well, 12-well, 24-well, and 96-well plates. Some known organ-on-a-chip applications use special hardware systems (these are either home-made or bought commercially). Such systems we refer to as "other"—and these can be named by the user themselves.

In some implementations, a currently active cell culture can be moved (e.g., passaged) from one culture vessel to the next by running through a protocol sequence as follows:

From active cultures (list or graph), the user can select a single or multiple cell cultures.

The user clicks "run protocol"—and selects the specific protocol sequence they want to perform.

In the protocol sequence, one of the steps can be to select a "destination vessel." The user selects the culture vessel (shown in FIG. 12A), and completes the steps.

After they complete the protocol sequence:

The active culture list is updated now displaying the new culture vessels (the previous one disappears from the list, but is still in the graph).

The graph is updated reflecting the vessel and vessel numbers chosen by the user.

Figure 12B:
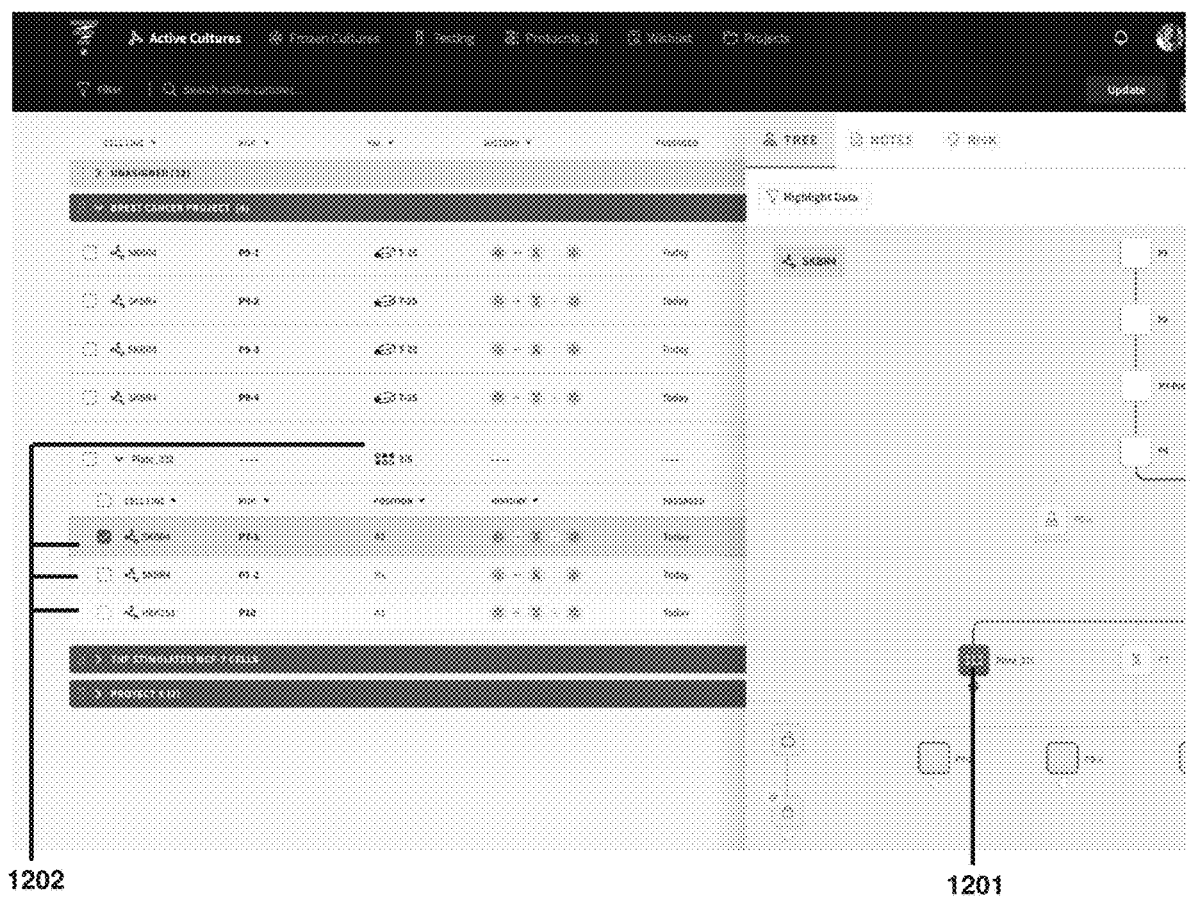

For multi-well plates, these are at first sight a single node as well, now with a special icon (FIG. 12B-1201). The user can hover/click over a node in the cell tree, and a schematic is displayed that indicates the well(s) the cell population is positioned. If other wells contain different cell lines, they are colored differently in this schematic. Merged cell models in a single well are displayed as two colors in some implementations.

In the case other cell lines are present in the well, the user can click on the other well and the other cell line tree can be displayed correspondingly.

In summary: the choice (and number) of destination vessels can be displayed in the system as part of:

the tree graph (either a single or multiple nodes are added, or a multi-well plate icon appears) (FIGS. 12-1201); and/or the list view of active cultures (FIGS. 12-1202), which displays a row for each culture vessel. The row displays the vessel type, the cell line name, and relevant characteristics.

Embodiments

The system allows the user to structure complex decision trees in the process of moving cell populations from one culture vessel to the variety of possible next destinations.

The system allows the user to track the process of moving cell populations from one culture vessel to the variety of possible next destinations.

The graphical representation allows the user to maintain a structured flow of information.

Examples of Ways the System Captures Destination Vessel Choice during the Passage protocol sequences:

In the system, users can choose and capture various situations that arise during cell culture maintenance as follows:

Situation 1 (FIG. 12A-1201 pointer with dotted line):

A single cell population is moved to a single new vessel (e.g., flask, dish, or other).

In the protocol sequences, the user can indicate in the "destination vessel" menu:

Choose Flask or Dish

Choose size

Done

This is a single row in the protocols screen.

Situation 2 (FIG. 12A-1202 Pointer with Dotted Line):

Two cell populations (from two independent cell line trees) are moved to a single new vessel (flask, dish, or other).

In the protocol sequences the user can indicate in the "destination vessel" menu:

For cell line 1:

Choose Flask or Dish

Choose size

Assign NAME "MY FLASK"

Done

For cell line 2:

Choose "MY FLASK"

Done

This flow captures a merge of two cell populations. This is recorded in the platform.

Situation 3 (FIG. 12A-1203):

A single cell population is moved to two new, independent vessels (e.g., flasks, dishes, or other).

In destination vessel menu:

Choose Flask or Dish [1]

Choose size

Click add

Choose Flask or Dish [2]

Choose size

Click add

Choose Flask or Dish [3]

Choose size

Done

This is a single row in the protocols screen. Once the protocol is complete/done, three nodes appear in the tree.

Situation 4 (FIG. 12A-1204):

A single cell population is moved to a single well in a 6-well plate:

Choose PLATE.

Choose 6-well

Click a single circle in the grid

View chosen coordinate: "A1"

Done

This is a single row in the protocols screen. Once the protocol is complete, one node appears in the tree displaying the multi-well icon. When the user hovers the mouse over the icon, a single circle is shown in contrasting color.

Situation 5 (not shown):

A single cell population is moved to three wells in a 6-well plate:
  Choose PLATE.
  Choose 6-well
  Click and drag 3 circles in the grid.
  View chosen coordinates: "A1—A3"
Done
This is a single row in the protocols screen. Once the protocol is complete/done, one node appears in the tree, displaying the multi-well icon and when the user hovers the mouse over the icon, three dots are shown in contrasting color).
Situation 6 (FIG. 12A-1205 pointers with dotted line):
Two cell populations from two independent trees are moved into two individual wells in a 6-well plate:
For the cell population from cell line tree 1:
  Choose PLATE
  Choose 6-well.
  Assign NAME "MY_PLATE 2"
  Click a single circle in the grid
  View chosen coordinate: "A1"
For the cell population from cell line tree 2:
  Choose "MY_PLATE 2"
  The position already assigned a name is shown in a contrasting color, the user sees which positions are not yet assigned a cell population. Click a single circle in the grid in a position not yet assigned a cell population (A2, A3, B1, B2, B3).
  View chosen coordinate: "B1"
Done
These are two rows in the protocols screen, until the protocol is COMPLETE/done. After completion these are collapsed into a single node, displaying the multi-well icon and when the user hovers the mouse over the icon two dots are shown in two distinct, contrasting colors. The node with the multi-well icon is displayed in the tree for cell line 1 as well as in the tree for cell line 2. An example is shown in FIG. 12B for a multi-well, and three occupied cell populations.
  In the active cell culture list, the multi-well is shown. Top bar shows all occupied positions (FIG. 12B-top line 1202).
  Expanding the row gives for each occupied well what cell line/cell population in there at that moment.
Below:
Situation 7:
Two cell populations from different cell lines are moved into a single well in a 6-well plate (another example of a merge):
For the cell population from cell line tree 1:
  Choose PLATE
  Choose 6-well
  Assign name "MY_PLATE_3"
  Click a single circle in the grid
  View chosen coordinate: "A1"
For the cell population from cell line tree 2:
  Choose "MY_PLATE_3"
  The position already assigned a cell population is shown in a contrasting color, the user sees which positions are not yet assigned a cell population. The user can click on the position already assigned a cell population. The color of the well should change to indicate two cells are now in a single culture vessel. The user can correct this if this is a mistake.
  View chosen coordinate: "A1, A1"
Done
These are two rows in the protocols screen, until the protocol is complete/done. After completion these are collapsed into a single node, displaying the multi-well icon and when the user hovers the mouse over the icon a single filled dot is shown in a merge color. The node with the multi-well icon is displayed in the tree for cell line 1 as well as in the tree for cell line 2.
Situation 8:
Two cell populations are passaged into an unknown vessel type (another example of a merge):
For the cell population from cell line tree 1:
  Choose "OTHER".Give name: "MY_UNIQUE_VESSEL_5"
For the cell population from cell line tree 2:
  Choose "MY_UNIQUE_VESSEL_5"
Done
This can be used for applications such as organ-on-a-chip and other multi-cellular in vitro systems that resemble the human physiology.

Example of Freeze Protocol Sequence

A single cell population is moved to a cryotube:
In the protocol sequences the user can indicate in the "destination vessel" menu:
  Choose number of cryotubes
  Choose box name (location of box in the freezer)
  Choose position in box
Done
  Combinations of the foregoing concepts and additional concepts discussed here (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.
  The skilled artisan will understand that the drawings primarily are for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).
  To address various issues and advance the art, the entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. As such, all examples and/or embodiments are deemed to be non-limiting throughout this disclosure.
  It is to be understood that the logical and/or topological structure of any combination of any program components (a component collection), other components and/or any present feature sets as described in the Figures and/or throughout are not limited to a fixed operating order and/or arrangement, but rather, any disclosed order is an example and all equivalents, regardless of order, are contemplated by the disclosure.
  Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices;

magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a processor, a field programmable gate array (FPGA), and/or an application specific integrated circuit (ASIC). Software modules (executed on hardware) can include instructions stored in a memory that is operably coupled to a processor, and can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The terms "instructions" and "code" should be interpreted broadly to include any type of computer-readable statement (s). For example, the terms "instructions" and "code" may refer to one or more programs, routines, sub-routines, functions, procedures, etc. "Instructions" and "code" may include a single computer-readable statement or many computer-readable statements.

While specific embodiments of the present disclosure have been outlined above, many alternatives, modifications, and variations will be apparent to those skilled in the art. Accordingly, the embodiments set forth herein are intended to be illustrative, not limiting.

The invention claimed is:

1. A method, comprising:
   generating, at a processor, a first node of a directed tree, the first node digitally representing a first cell population of a cell line;
   receiving, at the processor, an indication that a user is to perform a protocol on the first cell population that will generate a second cell population of the cell line;
   automatically generating, at the processor, a second node of the directed tree, the second node (1) being a child node of the first node and (2) digitally representing the second cell population, the first node being connected to the second node in the directed tree via an edge;
   causing, at the processor and after receiving an indication that the user has performed the protocol on the first cell population to generate the second cell population, first data to be stored at the edge, the first data being a transformation of the protocol used to generate the second cell population;
   causing, at the processor and after receiving an indication that the user has performed an update that is associated with the second cell population and that is not a protocol on the first cell population or the second cell population, second data to be stored at the second node, the first data and the second data being associated with phenotype changes in the cell line;
   receiving, at the processor, an indication of a set of information that is included in at least one of the first node, the second node, or the edge, and that is to be excluded from reports;
   generating, at the processor, a report that summarizes information included in the at least one of the first node, the second node, or the edge and that excludes the set of information; and
   sending, from the processor, a signal to cause display of the report within a user interface.

2. The method of claim 1, wherein receiving the indication that the user is to perform the protocol includes:
   sending, from the processor, a signal to cause display of a default protocol associated with the cell line; and
   receiving, at the processor, an indication of a change to the default protocol by the user, the change to the default protocol defining the protocol.

3. The method of claim 1, wherein receiving the indication that the user is to perform the protocol includes:
   sending, from the processor, a signal to cause display of a default protocol associated with the cell line; and
   receiving, at the processor, an indication of no change to the default protocol by the user, the default protocol being the protocol after receiving the indication of no change to the default protocol.

4. The method of claim 1, wherein the protocol is a first protocol and the method further comprises:
   causing, at the processor and after the user has performed the first protocol, the first protocol to be a default protocol for the cell line;
   receiving, at the processor, an indication that the user is to perform a second protocol on at least one of the first cell population or the second cell population; and
   sending, at the processor and automatically in response to receiving the indication that the user is to perform the second protocol, a signal to cause display of the default protocol.

5. The method of claim 1, wherein the protocol includes a sequenced set of key: value pairs.

6. The method of claim 1, further comprising:
   causing, via the processor, data associated with the first node, the second node, and the edge to be provided to an artificial intelligence (AI) model configured to generate an output predicting cell line behavior in relation to protocol choices indicated in the processor.

7. The method of claim 1, wherein the first cell population has active culture status when the indication that the user is to perform the protocol is received.

8. The method of claim 1, wherein the first cell population has frozen culture status when the indication that the user is to perform the protocol is received.

9. The method of claim 1, wherein the protocol is a first protocol and the edge is a first edge, the method further comprising:
   receiving, at the processor, an indication that the user is to perform a second protocol on the second cell population that will generate a third cell population of the cell line;
   generating, at the processor, a third node of the directed tree that digitally represents the third cell population and that is a child node of the second node, the directed tree including a second edge that digitally represents a connection between the second node and the third node;
   causing, at the processor and after the user has performed the protocol on the second cell population to generate the third cell population, data associated with the second protocol to be stored at the second edge;
   receiving, at the processor, a request for cell provenance information; and
   generating, at the processor, the cell provenance information based on the data associated with the first protocol at the first edge, and the data associated with the second protocol at the second edge.

10. The method of claim 1, wherein the protocol is a first protocol and the edge is a first edge, the method further comprising:
    receiving, at the processor, an indication that the user is to perform a second protocol on the second cell population that will generate a third cell population of the cell line;
    generating, at the processor, a third node of the directed tree that digitally represents the third cell population and that is a child node of the second node, the directed tree including a second edge that digitally represents a connection between the second node and the third node;
    causing, at the processor and after the user has performed the protocol on the second cell population to generate the third cell population, data associated with the second protocol to be stored at the second edge;
    receiving, at the processor, a request for cell provenance information; and generating, at the processor, the cell provenance information based on the data associated with the first node, the first protocol at the first edge, the second node, the data associated with the second protocol at the second edge, and the third node.

11. The method of claim 1, wherein the protocol is a first protocol and the edge is a first edge, the method further comprising:
receiving, at the processor, an indication that the user is to perform a second protocol on the second cell population that will generate a third cell population of the cell line;
generating, at the processor, a third node of the directed tree that digitally represents the third cell population and that is a child node of the second node, the directed tree including a second edge that digitally represents a connection between the second node and the third node;
causing, at the processor and after receiving an indication that the user has performed the protocol on the second cell population to generate the third cell population, data associated with the second protocol to be stored at the second edge;
receiving, at the processor, a request for cell provenance information;
generating, at the processor, the cell provenance information based on the data associated with the first node, the first protocol at the first edge, the second node, the data associated with the second protocol at the second edge, and the third node;
receiving, at the processor, an indication of a set of information associated with at least one of the first node, the second node, the third node, the first edge or the second edge, and that is to be excluded from reports; and
generating, at the processor, a report that summarizes information included in the at least one of the first node, the second node, the third node, the first edge or the second edge and that excludes the set of information.

12. An apparatus, comprising:
a memory; and
a processor operatively coupled to the memory and configured to:
receive an indication that a user plans to generate a second cell population of a cell line based on a first cell population of the cell line, the first cell population digitally represented by a first node in a directed tree;
send, automatically in response to receiving the indication that the user plans to generate the second cell population, a signal to cause display of a default protocol associated with the cell line;
receive, based on input from the user, an indication of a change to the default protocol that generates a modified protocol;
generate a second node that (1) is a child node of the first node, (2) is connected to the first node via an edge in the directed tree, and (3) digitally represents the second cell population;
cause, after receiving an indication that the user has performed the modified protocol on the first cell population, first data associated with the modified protocol to be stored at the edge;
cause after receiving an indication that the user has performed an update that is associated with the second cell population and that is not a modified protocol on the first cell population, second data associated with the second node,
the first data and the second data being associated with phenotype changes in the cell line;
receive an indication of a set of information that is included in at least one of the first node, the second node, or the edge, and that is to be excluded from reports;
generate a report that summarizes information included in the at least one of the first node, the second node, or the edge and that excludes the set of information; and
send a signal to cause display of the report within a user interface.

13. The apparatus of claim 12, wherein the processor is further configured to:
receive, after storing the data associated with the modified protocol at the edge, an indication that the user plans to generate a third cell population of the cell line; and
send, automatically in response to receiving the indication that the user plans to generate the third cell population, a signal to cause display of the modified protocol.

14. The apparatus of claim 12, wherein the edge is a first edge and the processor is further configured to:
receive an indication that the user is to perform a protocol on the first cell population that will generate a third cell population of the cell line;
generate a third node that (1) is a child node of the first node, (2) is connected to the first node via a second edge in the directed tree, and (3) digitally represents the third cell population; and
cause, after the user has performed the protocol on the first cell population to generate the third cell population, data associated with the protocol to be stored at the second edge.

15. The apparatus of claim 12, wherein the edge is a first edge and the processor is further configured to:
receive an indication that the user is to perform a protocol on the second cell population that will generate a third cell population of the cell line;
generate a third node that (1) is a child node of the second node, (2) is connected to the second node via a second edge of the directed tree, and (3) digitally represents the third cell population; and
cause, after the user has performed the protocol on the first cell population to generate the third cell population, data associated with the protocol to be stored at the second edge.

16. The apparatus of claim 12, wherein the processor is further configured to:
cause data associated with the first node, the second node, and the edge to be provided to an artificial intelligence (AI) model configured to generate an output predicting how protocol steps and modifications can affect risks of cell error.

17. The apparatus of claim 12, wherein the first cell population has one of active culture status or frozen culture status.

18. A non-transitory processor-readable medium storing code representing instructions to be executed by a processor, the code comprising code to cause the processor to:
receive an indication that a user plans to generate a second cell population of a cell line based on a first cell population of the cell line, the first cell population digitally represented by a first node in a directed tree;
send, automatically in response to receiving the indication that the user plans to generate the second cell population, a signal to cause display of a default protocol associated with the cell line;

receive, based on input from the user, an indication that the default protocol will not be modified;

generate a second node that (1) is a child node of the first node, (2) is connected to the first node via an edge in the directed tree, and (3) digitally represents the second cell population;

cause, after receiving an indication that the user has performed the default protocol on the first cell population, first data associated with the default protocol to be stored at the edge;

cause, after receiving an indication that the user has performed an update that is associated with the second cell population and that is not a protocol on the first cell population, second data stored at the second node, the first data and the second data being associated with phenotype changes in the cell line;

receive an indication of a set of information that is included in at least one of the first node, the second node, or the edge, and that is to be excluded from reports;

generate a report that summarizes information included in the at least one of the first node, the second node, or the edge and that excludes the set of information; and send a signal to cause display of the report within a user interface.

19. The non-transitory processor-readable medium of claim 18, wherein the code further comprises code to cause the processor to:

receive an indication that the user plans to generate a third cell population of the cell line based on one of the first cell population or the second cell population; and send, automatically and in response to receiving the indication that the user plans to generate the third cell population, a signal to cause display of the default protocol.

20. The non-transitory processor-readable medium of claim 18, wherein the code further comprises code to cause the processor to:

generate cell provenance information based on the data associated with the default protocol at the edge and less structured data stored in the nodes.

21. The non-transitory processor-readable medium of claim 18, wherein the protocol and modified protocol includes a sequenced set of actions.

* * * * *